(12) United States Patent
Ziegler

(10) Patent No.: US 7,491,211 B2
(45) Date of Patent: Feb. 17, 2009

(54) MEDICAL RETRIEVAL DEVICES

(75) Inventor: Dave Ziegler, Bedford, IN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 780 days.

(21) Appl. No.: 10/853,052

(22) Filed: May 25, 2004

(65) Prior Publication Data

US 2005/0277947 A1    Dec. 15, 2005

(51) Int. Cl.
A61B 17/22 (2006.01)
(52) U.S. Cl. ...................................... 606/127
(58) Field of Classification Search ................ 606/113, 606/114, 127, 159, 200
See application file for complete search history.

(56) References Cited

U.S. PATENT DOCUMENTS

| | | | |
|---|---|---|---|
| 1,054,960 A | 3/1913 | Butner | |
| 3,787,081 A | 1/1974 | Macy | |
| 3,791,387 A | 2/1974 | Itoh | |
| 4,046,150 A | 9/1977 | Schwartz et al. | |
| 4,203,429 A | 5/1980 | Vasilevsky et al. | |
| 4,611,594 A | 9/1986 | Grayhack et al. | |
| 4,632,100 A * | 12/1986 | Somers et al. | 606/232 |
| 4,633,871 A | 1/1987 | Shinozuka | |
| 4,691,705 A | 9/1987 | Okada | |
| 4,807,626 A | 2/1989 | McGirr | |
| 5,057,114 A | 10/1991 | Wittich et al. | |
| 5,064,428 A | 11/1991 | Cope et al. | |
| 5,084,054 A | 1/1992 | Bencini et al. | |
| 5,098,441 A | 3/1992 | Wechler | |
| 5,171,233 A | 12/1992 | Amplatz et al. | |
| 5,207,686 A | 5/1993 | Dolgin | |
| 5,330,482 A | 7/1994 | Gibbs et al. | |
| 5,421,832 A | 6/1995 | Lefebvre | |
| 5,480,406 A | 1/1996 | Nolan et al. | |
| 5,484,384 A | 1/1996 | Fearnot | |
| 5,496,330 A | 3/1996 | Bates et al. | |
| 5,499,981 A | 3/1996 | Kordis | |
| 5,725,525 A | 3/1998 | Kordis | |
| 5,895,352 A | 4/1999 | Kleiner | |
| 5,989,266 A | 11/1999 | Foster | |

(Continued)

FOREIGN PATENT DOCUMENTS

DE     29 00 265 A1    7/1980
DE     197 03 482      8/1998

(Continued)

OTHER PUBLICATIONS

42ND Brighton (Saltdean) Scout Group, Uk, "Get Knotted! Animated Knots for Scouts", [online], available at: URL http://www.mistral.co.uk/42brghton/knots/42ktmenu.html>, [last accessed on May 17, 2004].

(Continued)

*Primary Examiner*—Kevin T Truong
(74) *Attorney, Agent, or Firm*—Finnegan Henderson Farabow Garrett & Dunner, L.L.P.

(57) ABSTRACT

A medical retrieval device includes a retrieval assembly comprising a plurality of filaments knotted together at a distal end of the retrieval assembly. The knotted distal end provides the device with an atraumatic distal tip. Various knotting arrangements can be used at the knotted distal end. The retrieval assembly can be collapsed when restrained and expanded when unrestrained.

22 Claims, 23 Drawing Sheets

U.S. PATENT DOCUMENTS

| | | | |
|---|---|---|---|
| 6,063,113 A * | 5/2000 | Kavteladze et al. | 606/200 |
| 6,159,220 A | 12/2000 | Gobron et al. | |
| 6,302,895 B1 | 10/2001 | Gobron et al. | |
| 2004/0122445 A1 | 6/2004 | Butler et al. | |

FOREIGN PATENT DOCUMENTS

| | | |
|---|---|---|
| EP | 0 477 020 A1 | 3/1992 |
| EP | 0 765 636 | 4/1997 |
| WO | WO 98/36694 | 8/1998 |
| WO | WO 99/08607 | 2/1999 |

OTHER PUBLICATIONS

"How to Tie Knots: Scout Traditional Scouting", [online], available at: URLhttp://www.inquiry.net/outdoor/skills/b-p/knots.htm>, [last accessed on May 17, 2004].

"Roper's Knot Pages—Stoppers. Knots on the end of a rope", [online], available at: URLhttp://www.realknots.com/knots/stoppers.htm>, [last accessed on Mar. 13, 2003].

"Roper's Knot Pages—Bends", [online], available at: URLhttp://www.realknots.com/knots/bends.htm>, [last accessed on Mar. 13, 2003].

A. Semjonow, M. Brandt, H. Reul, P. Rathert, "Surface of Knots and Knot Holding Capacity In Polypropylene Monofilaments," Biomedizinische Technik, vol. 38, No. 1 / 2, Jan. 1993, pp. 21-24.

International Search Report for International Application No. PCT/US2005/016536, dated Sep. 15, 2005.

Written Opinion of the International Searching Authority for International Application No. PCT/US2005/016536, dated Sep. 15, 2005.

* cited by examiner

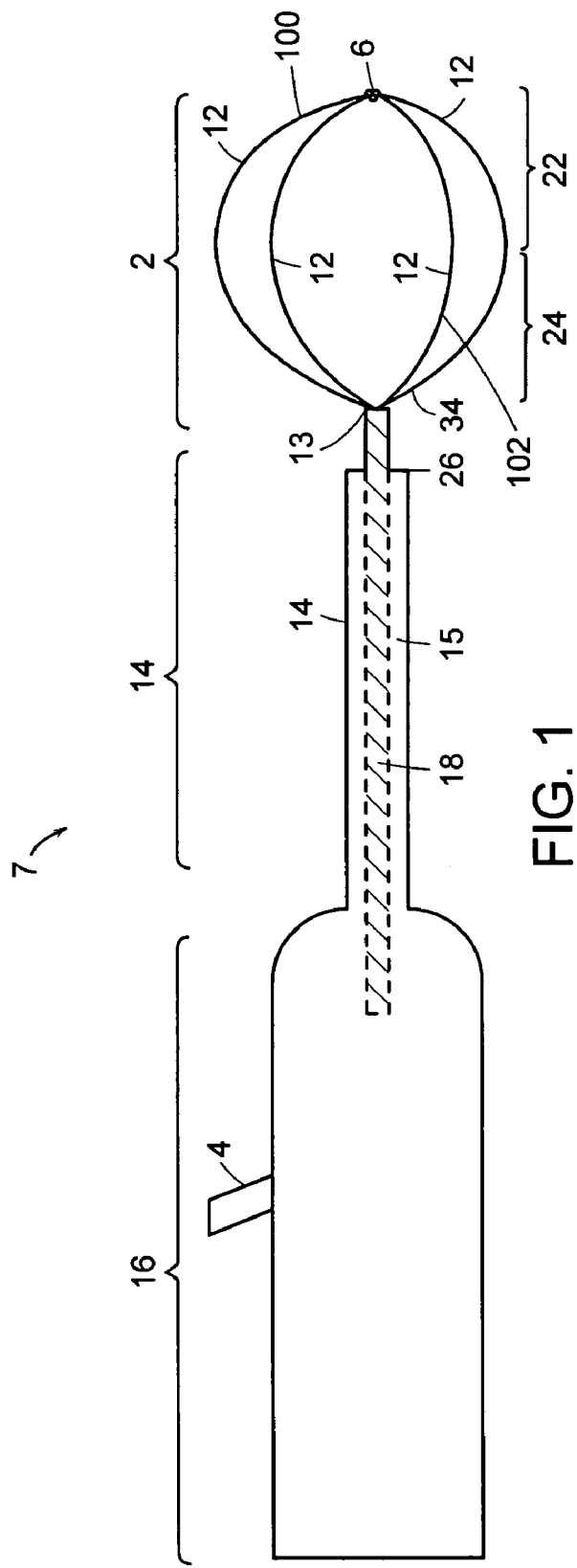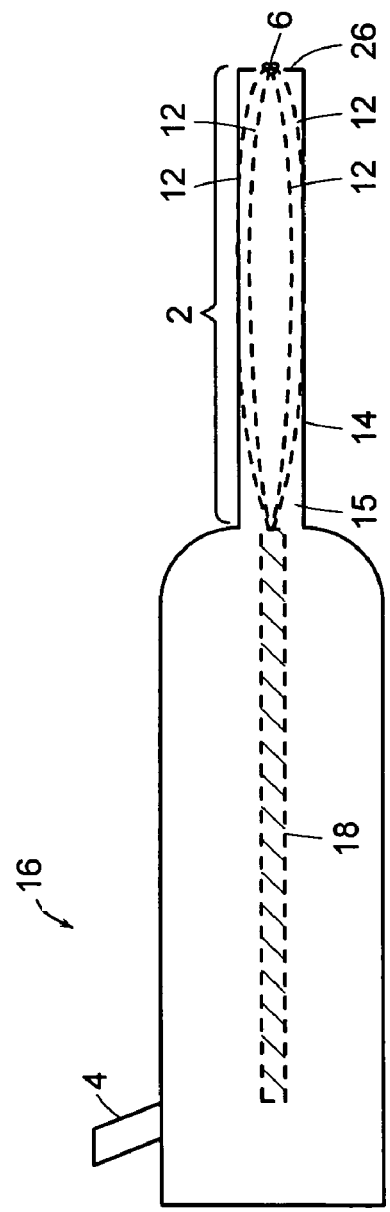
FIG. 1
FIG. 2

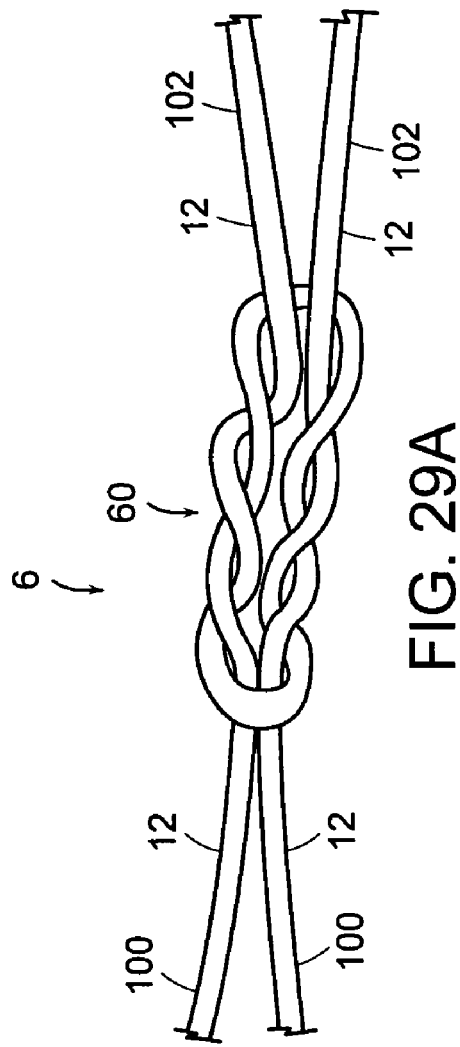
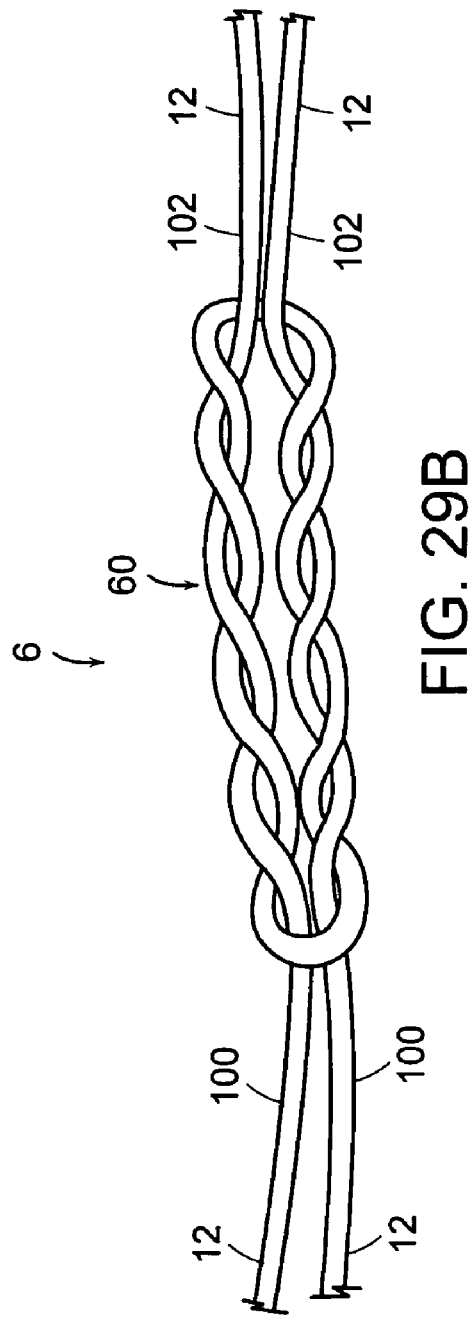

MEDICAL RETRIEVAL DEVICES

TECHNICAL FIELD

The invention generally relates to medical retrieval devices such as those with retrieval assemblies for retrieving material from the body of a mammal.

BACKGROUND INFORMATION

Certain medical procedures and treatments involve the use of retrieval devices with retrieval assemblies for capturing material from within bodies of patients, such as kidney stones and/or other materials. Commonly, these retrieval assemblies, such as, for example, basket assemblies, are constructed using multiple filaments such that a basket having a plurality of legs is formed.

SUMMARY OF THE INVENTION

The ends of a retrieval assembly may be formed by twisting or knotting filaments together at the distal end of the retrieval assembly. Certain knots can be difficult to make at least in part because they are difficult to tie. Certain knots also may fail to fix the radial position of the filaments, resulting in "play" and/or unintended angles between the filaments. As a result, damage to the filaments and operator fatigue during manufacture of the retrieval assembly wastes materials and increases manufacturing time.

The invention generally relates to various types of knots at the distal end of a medical device retrieval assembly, such as a basket assembly. The basket assembly has an atraumatic tip, in that the tip does not have any significant distal protrusion or outward projection that can poke tissue, pierce tissue, otherwise cause trauma to tissue, or inhibit or hinder capturing of material from within the body of a patient. The knots at the distal end of the basket assembly generally fix the position of the filaments that are tied together to form the knots, and the knots help to prevent unintended angles from forming between the filaments. The knots also allow for retrieval assemblies to have an odd or even number of legs.

In one aspect, the invention generally involves a medical retrieval device comprising a sheath and a retrieval assembly. The retrieval assembly includes a plurality of filaments knotted together in a flipped double overhand knot to form a knotted distal end of the retrieval assembly. The retrieval assembly is collapsed when restrained by the sheath and expanded when unrestrained by the sheath.

In a related aspect, the invention generally involves a method of making a flipped double overhand knot at the distal end of a retrieval assembly. The method includes providing a first filament comprising a first end and a second end, and providing a second filament comprising a first end and a second end. The second filament is laid across and substantially perpendicular to the first filament. The second end of the first filament is placed across the first end of the first filament and a first overhand knot is tied with the first filament around the second filament. The second end of the second filament is placed across the first end of the second filament and a second overhand knot is tied with the second filament around the first filament to form the flipped double overhand knot at the distal end of the retrieval assembly. The invention comprises a retrieval device including such a retrieval assembly.

In another aspect, the invention generally involves a medical retrieval device comprising a sheath and a retrieval assembly. The retrieval assembly includes a plurality of filaments knotted together in a carrick bend knot to form a knotted distal end of the retrieval assembly. The retrieval assembly is collapsed when restrained by the sheath and expanded when unrestrained by the sheath.

In a related aspect, the invention generally features a method of making a carrick bend knot at the distal end of a retrieval assembly. The method comprises providing a first filament comprising a first end and a second end, and providing a second filament comprising a first end and a second end. The first filament is bent wherein the second end of the first filament crosses the first end of the first filament to form a first loop defining a lumen. The first loop is placed on top of the second filament. The second filament is bent wherein the first end of the second filament crosses the second end of the first filament and is placed under the first end of the first filament to form a second loop. The first end of the second filament is placed through the lumen of the first loop and under the second filament, and the first end of the second filament is pulled through the lumen of the first loop to form the carrick bend knot at the distal end of the retrieval assembly.

Another aspect of the invention generally relates to a medical retrieval device comprising a sheath and a retrieval assembly. The retrieval assembly includes a plurality of filaments knotted together in a water/webbing knot to form a knotted distal end of the retrieval assembly. The retrieval assembly is collapsed when restrained by the sheath and expanded when unrestrained by the sheath.

In a related aspect, the invention generally involves a method of making the water/webbing knot at the knotted distal end of the retrieval assembly. The method comprises providing three or more parallel filaments grouped together. An overhand knot is tied with the three or more parallel filaments to form the water/webbing knot at the knotted distal end of the retrieval assembly.

A further aspect of the invention generally features a medical retrieval device comprising a sheath and a retrieval assembly. The retrieval assembly comprises a plurality of filaments knotted together in a barrel knot to form a knotted distal end of the retrieval assembly. The retrieval assembly is collapsed when restrained by the sheath and expanded when unrestrained by the sheath.

A related aspect of the invention generally features a method of making the barrel knot at the knotted distal end of the retrieval assembly. The method includes providing a plurality of parallel filaments. The plurality of parallel filaments are coiled to form a first set of at least two loops, each loop defining a lumen. A first overhand knot is tied with the plurality of parallel filaments through the lumens of the first set of at least two loops to form the barrel knot at the knotted distal end of the retrieval assembly. In one embodiment, the plurality of parallel filaments are coiled to form a second set of at least two loops, each loop defining a lumen, and a second overhand knot is tied with the plurality of parallel filaments through the lumens of the second set of at least two loops.

In another related aspect, the invention generally involves a method of making the barrel knot at the knotted distal end of the retrieval assembly. The method includes providing a plurality of filaments grouped together. The grouped filaments are bent to form a loop defining a lumen wherein an end of the filaments crosses a portion of the filaments, and the end of the filaments are wound around the grouped filaments and through the lumen of the loop two or more times to form the barrel knot at the knotted distal end of the retrieval assembly.

In another aspect, the invention generally features a medical retrieval device comprising a sheath and a retrieval assembly. The retrieval assembly includes a plurality of filaments knotted together in a fisherman's knot to form a knotted distal end of the retrieval assembly. The retrieval assembly is collapsed when restrained by the sheath and expanded when unrestrained by the sheath.

In a related aspect, the invention generally involves a method of making the fisherman's knot at the knotted distal end of the retrieval assembly. In one embodiment, the method includes providing a first filament comprising a first end and a second end, and providing a second filament comprising a first end and a second end. A first overhand knot is tied around the second filament with the first end of the first filament. A second overhand knot is tied around the first filament with the second end of the second filament to form the fisherman's knot at the knotted distal end of the retrieval assembly. In another embodiment the method includes providing a plurality of filaments grouped together. The grouped filaments are bent to form a loop defining a lumen wherein an end of the filaments crosses a portion of the filaments. The end of the filaments are wound around the grouped filaments and through the lumen of the loop two or more times to form the barrel knot at the knotted distal end of the retrieval assembly.

In yet another aspect, the invention generally relates to a medical retrieval device comprising a sheath and a retrieval assembly. The retrieval assembly includes a plurality of filaments knotted together in a surgeon's knot to form a knotted distal end of the retrieval assembly. The retrieval assembly is collapsed when restrained by the sheath and expanded when unrestrained by the sheath.

A related aspect of the invention generally involves a method of making the surgeon's knot at the knotted distal end of the retrieval assembly. The method includes providing a first filament comprising a first end and a second end, and providing a second filament comprising a first end and a second end. The first filament is bent to form a first loop defining a lumen, wherein the first end of the first filament is substantially parallel to the second end of the first filament. The first loop is laid on top of and substantially perpendicular to the second filament. The first end of the second filament and the second end of the second filament are placed through the lumen of the first loop to form a second loop around the first filament. The second loop defines a lumen. The first end of the second filament is wound through the lumen of the first loop and around the first filament at least one time. The second end of the first filament is wound through the lumen of the second loop and around the second filament at least one time to form the surgeon's knot at the knotted distal end of the retrieval assembly.

In another related aspect, the invention generally features a method of making the surgeon's knot at the knotted distal end of the retrieval assembly by providing first and second filaments wherein the first filament is bent to form a first loop defining a lumen with a first end of the first filament being substantially parallel to a second end of the first filament. The first loop is laid on top of and substantially perpendicular to the second filament. A first end of the second filament and a second end of the second filament are placed through the lumen of the first loop to form a second loop around the first filament. The second loop defines a lumen. The second end of the second filament is wound through the lumen of the first loop and around the first filament at least one time. The first end of the first filament is wound through the lumen of the second loop and around the second filament at least one time to form the surgeon's knot at the knotted distal end of the retrieval assembly.

In another related aspect, the invention generally involves a method of making the surgeon's knot at the knotted distal end of the retrieval assembly by winding the first filament around the second filament at least three times and tying an overhand knot with the first end of the second filament and the second end of the first filament to form the surgeon's knot at the knotted distal end of the retrieval assembly.

In another aspect, the invention generally features a retrieval assembly comprising a flipped double overhand knot. The flipped double overhand knot includes a first filament comprising a first end and a second end and a second filament comprising a first end and a second end. The second filament is placed across and substantially perpendicular to the first filament. The second end of the first filament is placed across the first end of the first filament and a first overhand knot is tied with the first filament around the second filament. The second end of the second filament is placed across the first end of the second filament and a second overhand knot tied with the second filament around the first filament to form the flipped double overhand knot at the knotted distal end of the retrieval assembly.

A further aspect of the invention generally involves a retrieval assembly comprising a carrick bend knot. The carrick bend knot includes a first filament comprising a first end and a second end and a second filament comprising a first end and a second end. The first filament is bent wherein the second end of the first filament crosses the first end of the first filament to form a first loop defining a lumen. The first loop is placed on top of the second filament, and the second filament is bent wherein the first end of the second filament crosses the second end of the first filament and is placed under the first end of the first filament to form a second loop. The first end of the second filament is placed through the lumen of the first loop and under the second filament, and the first end of the second filament is pulled through the lumen of the first loop to form the carrick bend knot at the knotted distal end of the retrieval assembly.

In yet another aspect, the invention generally relates to a retrieval assembly comprising a water/webbing knot. The water/webbing knot includes three or more parallel filaments grouped together and an overhand knot is tied with the three or more parallel filaments to form the water/webbing knot at the knotted distal end of the retrieval assembly.

Another aspect of the invention generally features a retrieval assembly comprising a barrel knot. The barrel knot includes a plurality of parallel filaments, and the plurality of parallel filaments are coiled to form a first set of at least two loops, with each loop defining a lumen. A first overhand knot is tied with the plurality of parallel filaments through the lumens of the first set of at least two loops to form the barrel knot at the knotted distal end of the retrieval assembly.

In one embodiment, the barrel knot further comprises the plurality of parallel filaments coiled to form a second set of at least two loops, each loop defining a lumen, and a second overhand knot tied with the plurality of parallel filaments through the lumens of the second set of at least two loops.

In another aspect, the invention generally relates to a retrieval assembly comprising a barrel knot including a plurality of filaments grouped together, and the grouped filaments are bent to form a loop defining a lumen wherein an end of the filaments crosses a portion of the filaments. The end of the filaments is wound around the grouped filaments and through the lumen of the loop two or more times to form the barrel knot at the knotted distal end of the retrieval assembly.

Another aspect of the invention generally involves a retrieval assembly comprising a fisherman's knot. The fisherman's knot includes a first filament having a first end and a second end, and a second filament having a first end and a second end. A first overhand knot is tied around the second filament with the first end of the first filament and a second overhand knot is tied around the first filament with the second end of the second filament to form the fisherman's knot at the knotted distal end of the retrieval assembly.

In yet another aspect, the invention generally features a retrieval assembly comprising a surgeon's knot. The surgeon's knot includes a first filament comprising a first end and a second end, and a second filament comprising a first end and a second end. The first filament is bent to form a first loop defining a lumen, wherein the first end of the first filament is substantially parallel to the second end of the first filament. The first loop is laid on top of and substantially perpendicular to the second filament, and the first end of the second filament and the second end of the second filament is placed through the lumen of the first loop to form a second loop around the first filament, the second loop defining a lumen. The first end of the second filament is wound through the lumen of the first loop and around the first filament at least one time, and the second end of the first filament is wound through the lumen of the second loop and around the second filament at least one time to form the surgeon's knot at the knotted distal end of the retrieval assembly.

In another aspect, the invention generally relates to a retrieval assembly comprising a surgeon's knot having a first filament comprising a first end and a second end, and a second filament comprising a first end and a second end. The first filament is bent to form a first loop defining a lumen, wherein the first end of the first filament is substantially parallel to the second end of the first filament. The first loop is laid on top of and substantially perpendicular to the second filament, and the first end of the second filament and the second end of the second filament is placed through the lumen of the first loop to form a second loop around the first filament, the second loop defining a lumen. The second end of the second filament is wound through the lumen of the first loop and around the first filament at least one time, and the first end of the first filament is wound through the lumen of the second loop and around the second filament at least one time to form the surgeon's knot at the knotted distal end of the retrieval assembly.

In yet another aspect, the invention generally involves a retrieval assembly comprising a surgeon's knot including a first filament comprising a first end and a second end and a second filament comprising a first end and a second end. The first filament is wound around the second filament at least three times, and an overhand knot is tied with the first end of the second filament and the second end of the first filament to form the surgeon's knot at the knotted distal end of the retrieval assembly.

BRIEF DESCRIPTION OF THE DRAWINGS

In the drawings, like reference characters generally refer to the same parts throughout the different illustrations. The drawings are not necessarily to scale, emphasis instead generally being placed upon illustrating the principles of the invention.

FIG. 1 is a side plan view of a medical retrieval device with a medical retrieval assembly in a fully-extended or open position according to an illustrative embodiment of the invention.

FIG. 2 is a side plan view of the device depicted in FIG. 1 with the retrieval assembly in a collapsed/retracted position according to an illustrative embodiment of the invention.

FIGS. 29A-29B depict the surgeon's knot at the distal end of a medical retrieval assembly according to other illustrative embodiments of the invention.

DESCRIPTION

Figure 3:
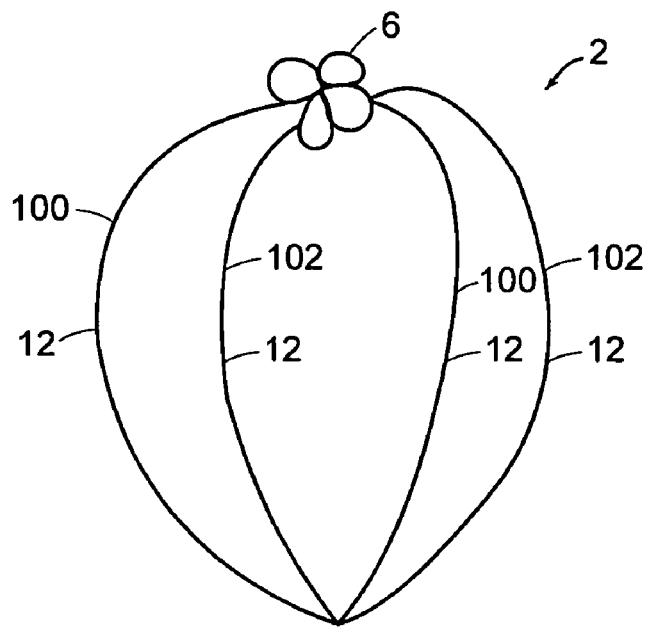
FIG. 3 depicts a four-leg basket according to an illustrative embodiment of the invention.

The invention is generally related to various types of knots and methods of making the knots that join filaments together at the distal end of a medical retrieval device, such as a medical retrieval basket. Any number of filaments may be used to form the knots, and additional filaments may be tied in or inserted through each of the knots. For example, a medical retrieval device according to the invention includes a retrieval assembly with filaments knotted together at their distal end. In one embodiment, the filaments also form legs of the retrieval assembly. Alternatively, the filaments form the distal end of the retrieval assembly and the legs are joined to the filaments. The knots generally fix the position of the filaments at the distal end of the retrieval assembly and prevent unintended angles from forming between the legs of the retrieval assembly. The medical retrieval devices, including the medical retrieval assemblies, have atraumatic tips, in that the tip does not have any significant distal protrusion or outward projection that can poke tissue, pierce tissue, or otherwise cause trauma to tissue or inhibit or hinder capturing of material from within the body of a patient.

The following are illustrative embodiments of the invention in which a medical retrieval device includes a substantially atraumatic retrieval assembly, for example, a retrieval basket, including a plurality of legs. The distal end of the retrieval assembly is formed by knotting together filaments.

FIG. 1 is a side plan view of a medical retrieval device 7 with a medical retrieval assembly 2 in a fully-extended or open position according to an illustrative embodiment of the invention. One feature of this embodiment of the retrieval device 7 for removing material from a body includes a handle 16, a sheath 14, and a retrieval assembly, such as basket 2. The handle 16, the sheath 14, and the retrieval assembly 2 are not shown in their correct size or proportion to each other. The sheath 14 typically is much longer than the handle 16 or the retrieval assembly 2 to allow insertion into a body cavity, canal, or tract. The retrieval assembly 2 can be made of resilient material, such as metal wires, forming three or more legs 12.

With continued reference to FIG. 1, the basket, or retrieval assembly 2 is the type that is collapsed within the sheath 14 for entry into the body. The sheath 14 has at least one lumen 15 therein, and it extends from the handle 16 to a distal sheath end 26. An elongated member 18 such as a cable, coil, shaft, guidewire, hollow tube, or mandril wire 18 extends within the lumen 15 from an actuating mechanism 4 in the handle 16 to a base 13 of the basket where the elongated member 18 joins to the basket base 13. Operation of the actuating mechanism 4 by an operator causes the basket 2 to move relative to the sheath 14 between a collapsed position within the sheath 14 as illustrated in FIG. 2, to an extended position outside of the sheath 14 where the basket 2 is open and extending beyond the distal end of the sheath 26 as shown in FIG. 1. When a hollow tube, for example, is the elongated member used within the sheath, other instruments, such as optical fibers and/or laser fibers, can be inserted into and extend through a lumen of the hollow tube for use in conjunction with the retrieval device.

Alternatively, the actuating mechanism 4 is operatively joined to the sheath 14. Thus, the actuating mechanism 4 causes movement of the sheath 14 to advance the sheath 14 over the stationary basket 2 and cable 18 combination, to thereby collapse the basket 2 within the sheath 14, and the actuating mechanism 4 slides the movable sheath 14 back to expose the stationary basket 2 and allow it to open/expand. Alternatively, a second actuating mechanism (not shown) is joined to the elongated member 18 and the sheath 14 and the basket 2 are actuated simultaneously. In general, these types of basket/sheath movement configurations and related handle mechanisms are known, and are seen in existing product designs available from, for example, Boston Scientific Corporation (Natick, Mass.).

FIG. 2 is a side plan view of the device 7 depicted in FIG. 1 with the retrieval assembly 2 in a collapsed/retracted position according to an illustrative embodiment of the invention. With the basket 2 restrained and collapsed within the sheath 14 as shown in FIG. 2, the sheath 14 is inserted into the body by an operator to a site in the body where the material to be retrieved is located (e.g., a stone in the ureter). By placing the retrieval assembly 2 in its unrestrained open/expanded position, as illustrated in FIG. 1, the basket 2 dilates the body tract in which it has been placed and can be manipulated by the operator to entrap or capture material within the basket 2. The basket 2 and/or the sheath 14 can then be moved to cause the legs 12 of the basket 2 to close around the material and capture it. According to one embodiment, the captured material may be fragmented by a lithotripsy (not shown) or crushed by the basket. Alternatively, the captured material is withdrawn from the body along with the sheath 14 and the basket 2 that is holding the material without fragmenting or crushing the captured material.

With continued reference to FIG. 1, in the illustrative embodiment, the basket 2 features a proximal end portion 24, a distal end portion 22, and an atraumatic tip 6. The tip 6, in accordance with the invention, is devoid of protrusions, fasteners, or outward projections. There is no adhesive necessary at the basket tip 6 to hold the basket legs 12 together as at least the basket tip 6 is formed by knotting filaments 100 and 102 together. However, in another embodiment, the filaments 100, 102 knotted together at the basket tip 6 are fixed by the application of an adhesive to the knot.

Figure 4:
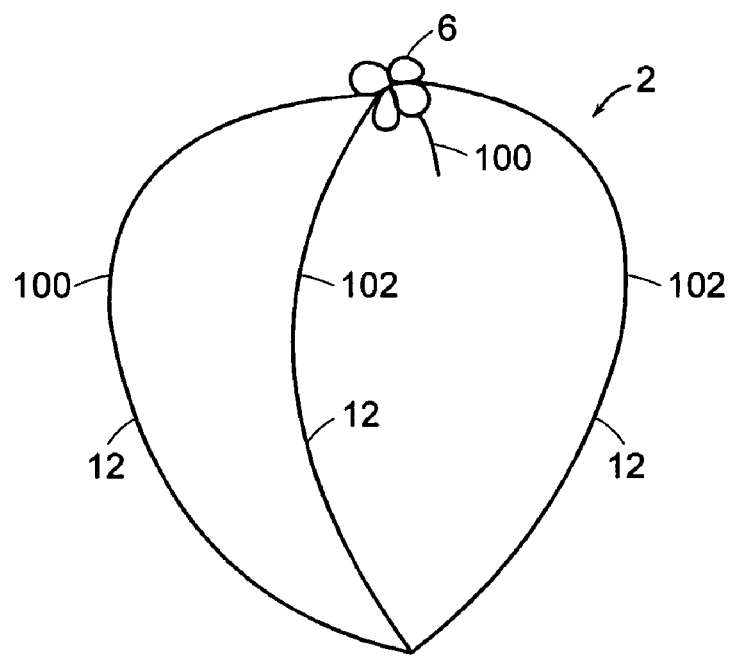
FIG. 4 depicts a three-leg basket according to an illustrative embodiment of the invention.

FIGS. 3 and 4 depict different embodiments of a retrieval assembly 2 including a plurality of legs 12. In the illustrated embodiments, the legs 12 of the retrieval assembly 2 are formed from the portions of the filaments 100, 102 extending from the knot at the tip 6. Alternatively, the legs 12 of the retrieval assembly 2 are joined to the filaments 100, 102. The distal end portion 22 of the retrieval assembly 2, thereby, is substantially atraumatic in that the tip 6 is devoid of outward projections or protrusions that might cause injury or trauma to tissue and/or that presents an impediment to contacting the tip 6 of the retrieval assembly 2 directly and intimately with tissue. In one embodiment, heat treatment, cold-forming, or other shaping processes using a ball-shaped die, for example, may be performed to shape the legs into a basket shape.

All of the following aspects and embodiments further have in common at least a first filament 100 and a second filament 102 which are knotted together to form the distal tip 6 of the medical retrieval assembly 2. In one embodiment according to the invention, referring now to FIG. 3, the filaments 100 and 102 are knotted at the distal tip 6 of the medical retrieval assembly 2, each filament 100 and 102 forming two legs 12 of the medical retrieval assembly 2. Retrieval assemblies 2 with a different number of odd (i.e., three) or even (i.e., four) number of legs 12 may also be constructed with the filaments 100, 102. A three leg retrieval assembly 2, for example, illustrated in FIG. 4, can be formed. In the illustrative embodiment, the three leg retrieval assembly 2 is formed by trimming away one of the two legs 12 formed by either filament 100, 102 at the distal tip 6. Alternatively, a three leg retrieval assembly can be formed by combining two legs together to form one leg (e.g., by twisting or braiding two or more legs together) (not shown).

Figure 5:
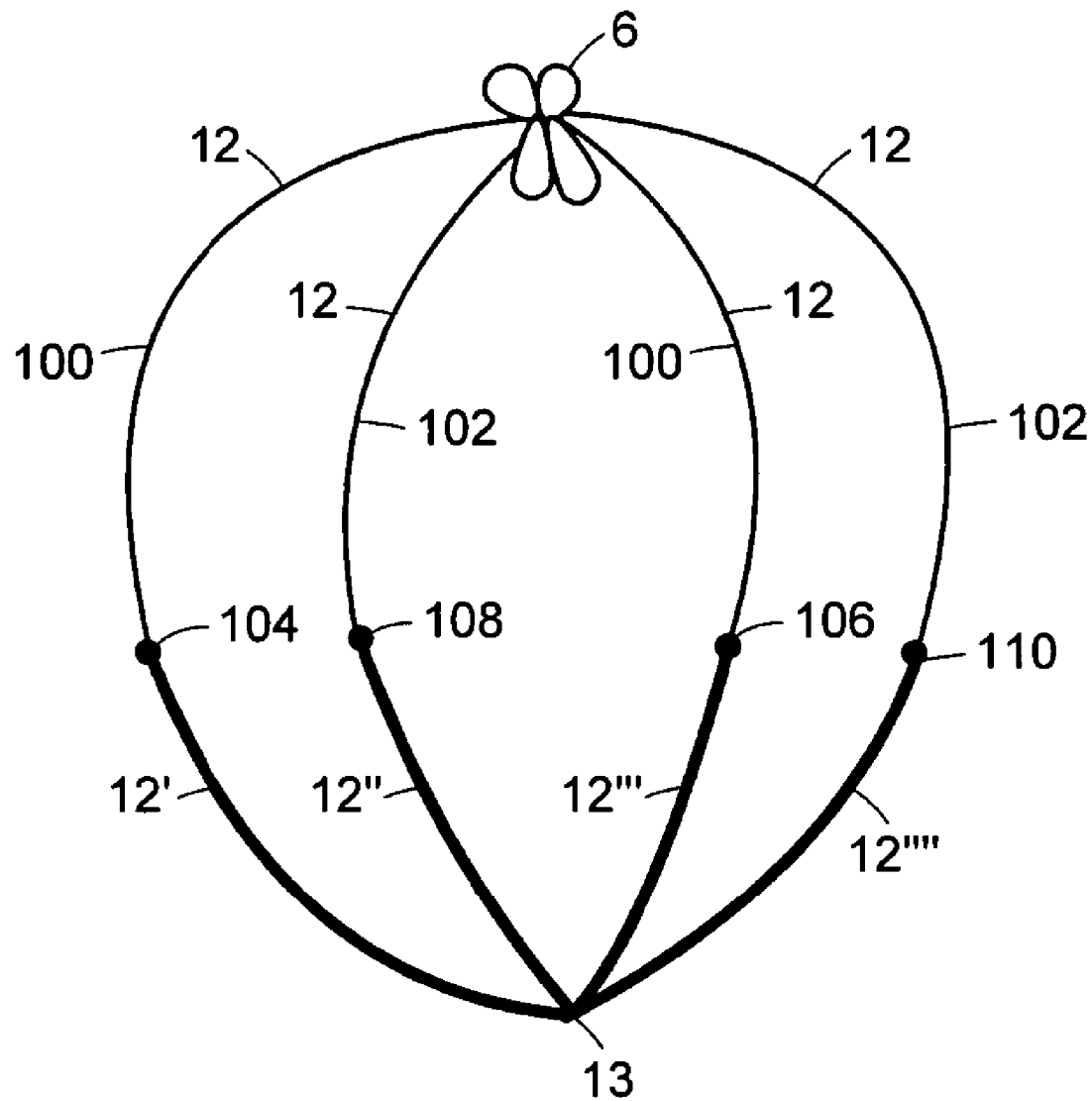
FIG. 5 depicts a four-leg basket according to another illustrative embodiment of the invention.

FIG. 5 depicts a four-leg retrieval assembly 2 including leg portions 12 formed from the filaments 100, 102 according to an illustrative embodiment of the invention. In the illustrative embodiment of the retrieval assembly 2, the first filament 100 includes a first end 104 and a second end 106, and the second filament 102 includes a first end 108 and a second end 110. As shown in FIG. 5, in a particular embodiment, the legs 12 of the retrieval assembly 2 include portions of the filaments 100 and 102 that are secured at their ends 104 and 106, and 102 and 108, respectively, to the ends of wires 12', 12", 12''', and 12''''. The unsecured ends of the wires 12', 12", 12''', and 12'''' are gathered together at the base 13 of the retrieval assembly 2.

In the illustrative aspects and embodiments for making the retrieval assembly 2 including a knot at the distal tip 6 according to the invention herein, the first filament 100 and the second filament 102 are initially positioned such that the first end 104 of the first filament 100 and the first end 108 of the second filament 102 correspond to a person's right hand side, and the second end 106 of the first filament 100 and the second end 110 of the second filament 102 correspond to a person's left hand side. This relative positioning is for illustrative purposes only, and alternate relative positions may be used to form each of the knots. The knots can be hand tied, as illustrated in the following embodiments, tied by any automated process, such as a machine, or tied by a combination of an automated and a manual process.

According to one embodiment, the filaments 100, 102 can be made of any biocompatible material, and any combination of biocompatible materials, including, for example, metals or metal alloys, such as stainless steel, nickel, and titanium, or cobalt and chromium alloys. In other embodiments, the filaments 100, 102 can comprise polymers such as, for example, polyester, Nomex®, Capton®, and PTFE (Teflon®). In a particular embodiment, the filaments 100, 102 are made of a shape memory material, such as nitinol. The filaments can be round or non-round, flexible, twisted, braided, roped or solid, and may comprise wires, extruded polymers, cords, or rope, and single layers, with sheathed multiple layers, and/or painted filaments.

Figure 6A:
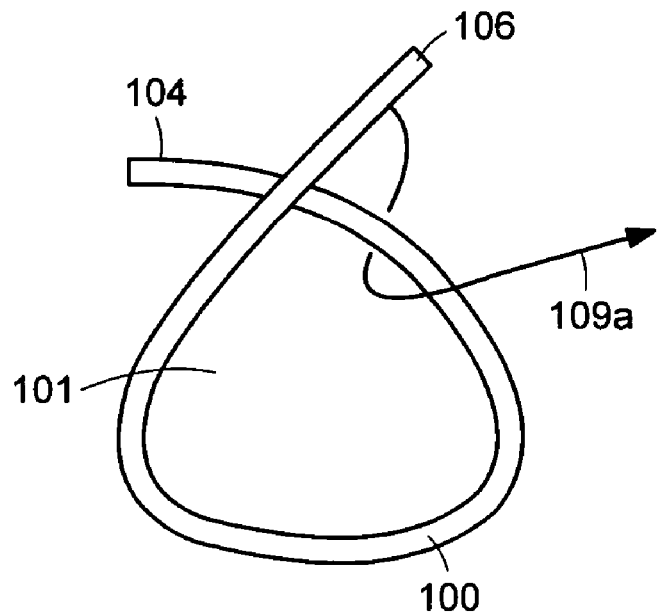
FIGS. 6A-6B depict the steps in constructing an embodiment of an illustrative overhand knot according to an illustrative embodiment of the invention.
Figure 6B:
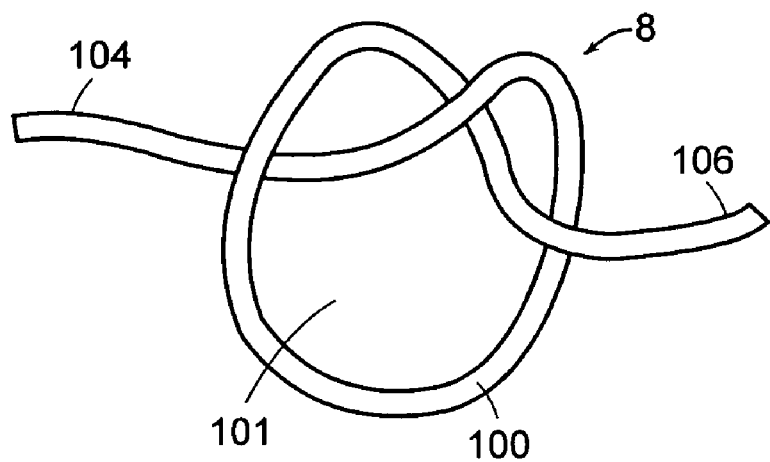

FIGS. 6A-6B depict the steps in constructing an embodiment of an illustrative overhand knot 8 according to an illustrative embodiment of the invention. According to the illustrative embodiment, the steps as shown in FIG. 6A include placing the second end 106 of the first filament 100 across the first end 104 of the first filament 100 to form a loop defining a lumen 101. As depicted in FIG. 6A, the second end 106 of the first filament 100 is wrapped around the first filament 100 in the direction of the arrow 109a and passed through the lumen 101 of the loop to exit the lumen 101 and form the overhand knot 8 illustrated in FIG. 6B.

Alternatively, the steps of forming an overhand knot 8 include placing the first end 104 of the first filament 100 across the second end 106 of the first filament 100, winding the second end 106 and pulling the first end 104 through the lumen 101 of the loop to exit the overhand knot 8 (not shown). These exemplary methods for forming an overhand knot 8 are for illustrative purposes only, and alternate methods of forming the overhand knot 8 may be used for the following embodiments of the invention.

Figure 7A:
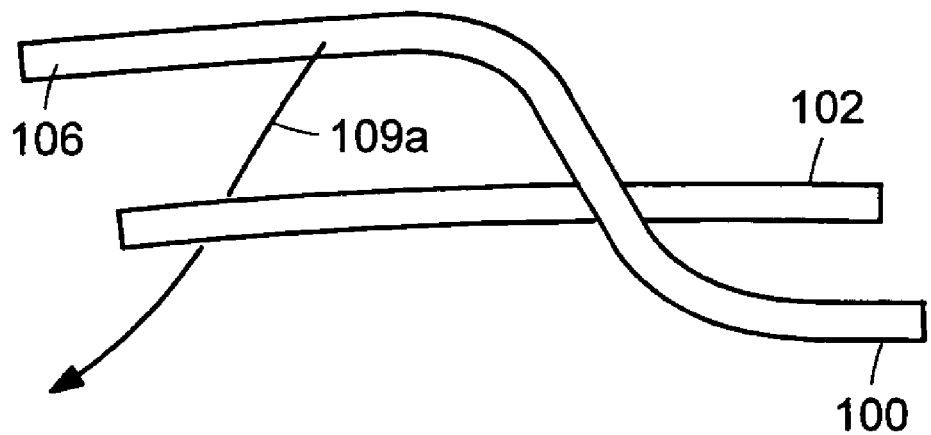
FIGS. 7A-7B depict the steps in winding a first filament around a second filament according to an illustrative embodiment of the invention.
Figure 7B:
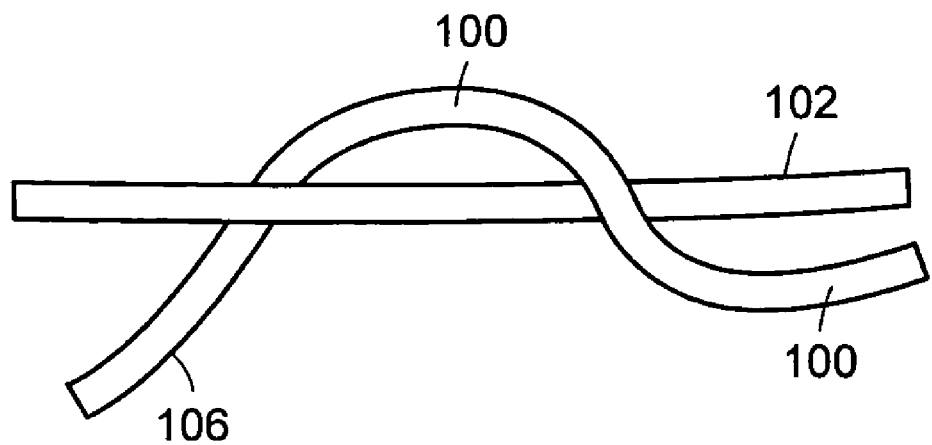

FIGS. 7A-7B depict exemplary steps in winding one filament around another filament according to an illustrative embodiment of the invention. For example, in the illustrative embodiment, the first filament 100 is placed across the second filament 102. The second end 106 of the first filament 100, depicted in FIGS. 7A and 7B, is wrapped around the second filament 102 in the direction of arrow 109a, such that the first filament 100 is wound around the second filament 102, illustrated in FIG. 7B. This exemplary method of winding the first filament 100 around the second filament 102 is for illustration only, and any alternate method of winding one filament around another filament or around another part of the same filament may also be used for the following embodiments of the invention.

Figure 8:
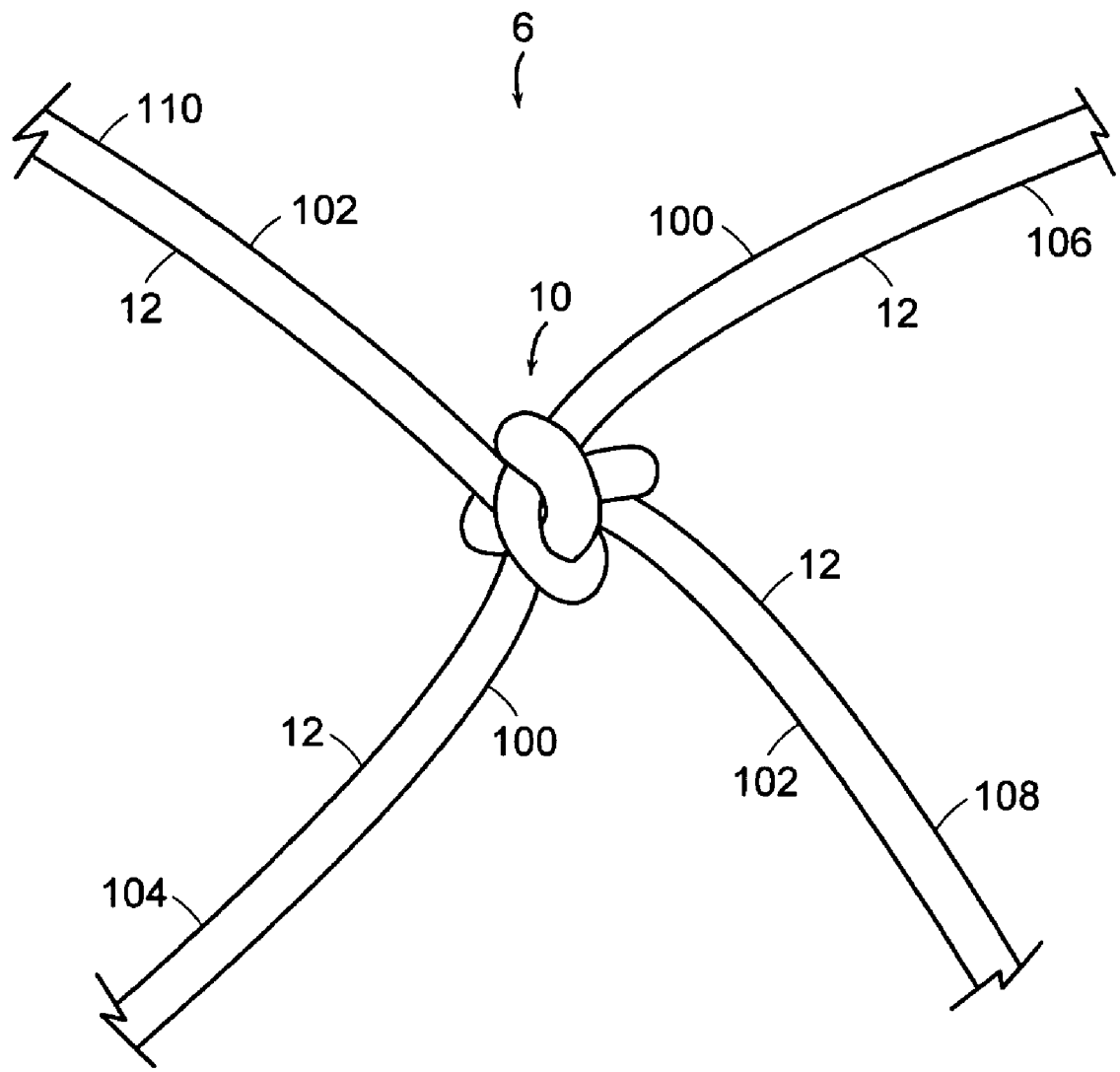
FIG. 8 depicts an end-view of a flipped double overhand knot at the distal end of a medical retrieval assembly according to an illustrative embodiment of the invention.

FIG. 8 depicts an end-view of a flipped double overhand knot 10 forming the distal tip 6 of a retrieval assembly 2 according to an illustrative embodiment of the invention. In the illustrative embodiment, the filaments 100, 102 of the retrieval assembly 2 exit the flipped double overhand knot 10 in a substantially symmetric pattern. However, the filaments 100, 102 may exit the knot in an asymmetrical pattern (not shown).

Figure 9A:
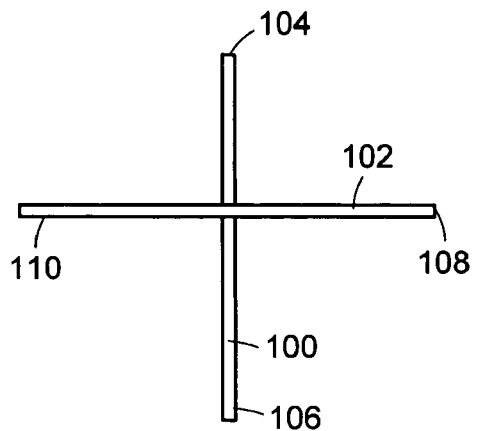
FIGS. 9A-9D depict the steps of making the flipped double overhand knot illustrated in FIG. 8 according to an illustrative embodiment of the invention.
Figure 9B:
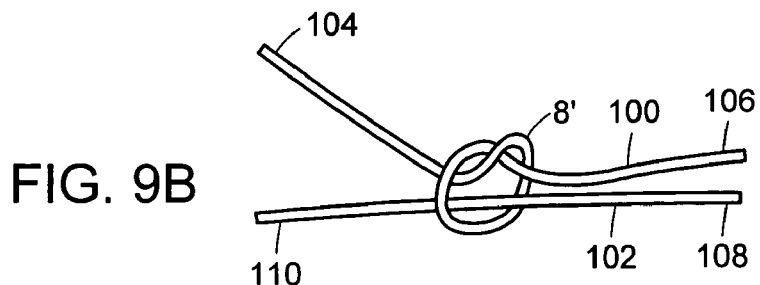
Figure 9C:
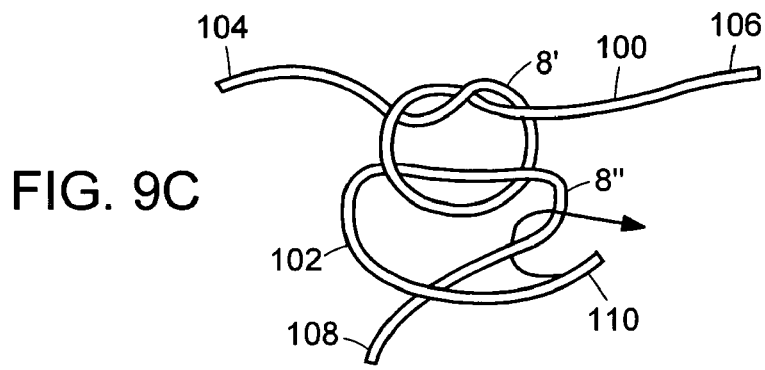
Figure 9D:
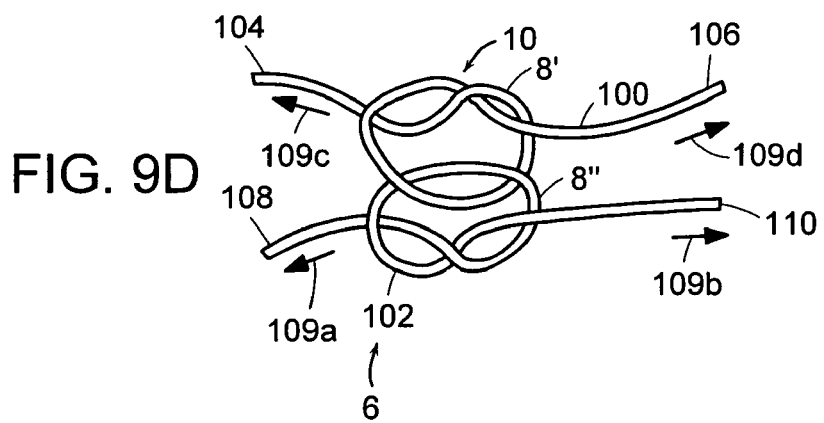

FIGS. 9A-9D depict an exemplary series of steps or stages in making the flipped double overhand knot 10 illustrated in FIG. 8 at the distal tip 6 of the retrieval assembly 2 according to an illustrative embodiment of the invention. In the exemplary embodiment depicted in FIG. 9A, the first step of the flipped double overhand method of forming the distal tip 6 of the retrieval assembly 2 includes laying the second filament 102 across and substantially perpendicular to the first filament 100. In the next step, shown in FIG. 9B, the second end 106 of the first filament 100 is placed across the first end 104 of the first filament 100 and a first single overhand knot 8' is tied in the first filament 100. The second filament 102 is secured thereby to the first filament 100. FIG. 9C depicts the next step of the flipped double overhand method, in which the second end 110 of the second filament 102 is placed across the first end 108 of the second filament 102 and a second single overhand knot 8" is tied in the second filament 102. The first single overhand knot 8' is thereby captured or linked to the second single overhand knot 8" to form the distal tip 6 of the retrieval assembly 2. The first end 108 and second end 110 of the second filament 102 can be pulled in the direction of the arrows 109a, 109b, and the first end 104 and second 106 of the first filament 100 can be pulled in the direction of the arrows 109c and 109d, indicated FIG. 9D, such that the first end 108 of the second filament 102 is substantially perpendicular to the first end 104 of the first filament 100, and the second end 110 of the second filament 102 is substantially perpendicular to the second end 106 of the first filament 100. In a particular embodiment of the retrieval assembly 2, an end of filaments 100 and 102 extending from the distal tip 6 can form at least a portion of a leg 12 as shown in FIG. 5.

Alternative methods (not shown) may also be used to form the distal tip 6 including the flipped double overhand knot 10. For example, the flipped double overhand knot 10 can be formed by laying the second filament 102 across and substantially perpendicular to the first filament 100. The first end 104 of the first filament 100 is then placed across the second end 106 of the first filament 100 and a first overhand knot 8' is tied around the second filament 102. The filaments 100, 102 are initially positioned such that the portion of the first overhand knot 8' in which the first end 104 of the first filament 100 crosses the second end 106 of the first filament 100 is facing upward from a flat planar surface. The filaments 100 and 102 can then be turned over and positioned such that the portion of the first overhand knot 8' in which the first end 104 of the first filament 100 crosses the second end 106 of the first filament 100 is facing downward toward the flat planar surface. The second end 110 of the second filament 102 is then placed across the first end 108 of the second filament 102 and a second overhand knot 8" is tied around the first filament 100. The first single overhand knot 8' is thereby captured or linked to the second single overhand knot 8" to form the distal tip 6 of the retrieval assembly 2.

Figure 10:
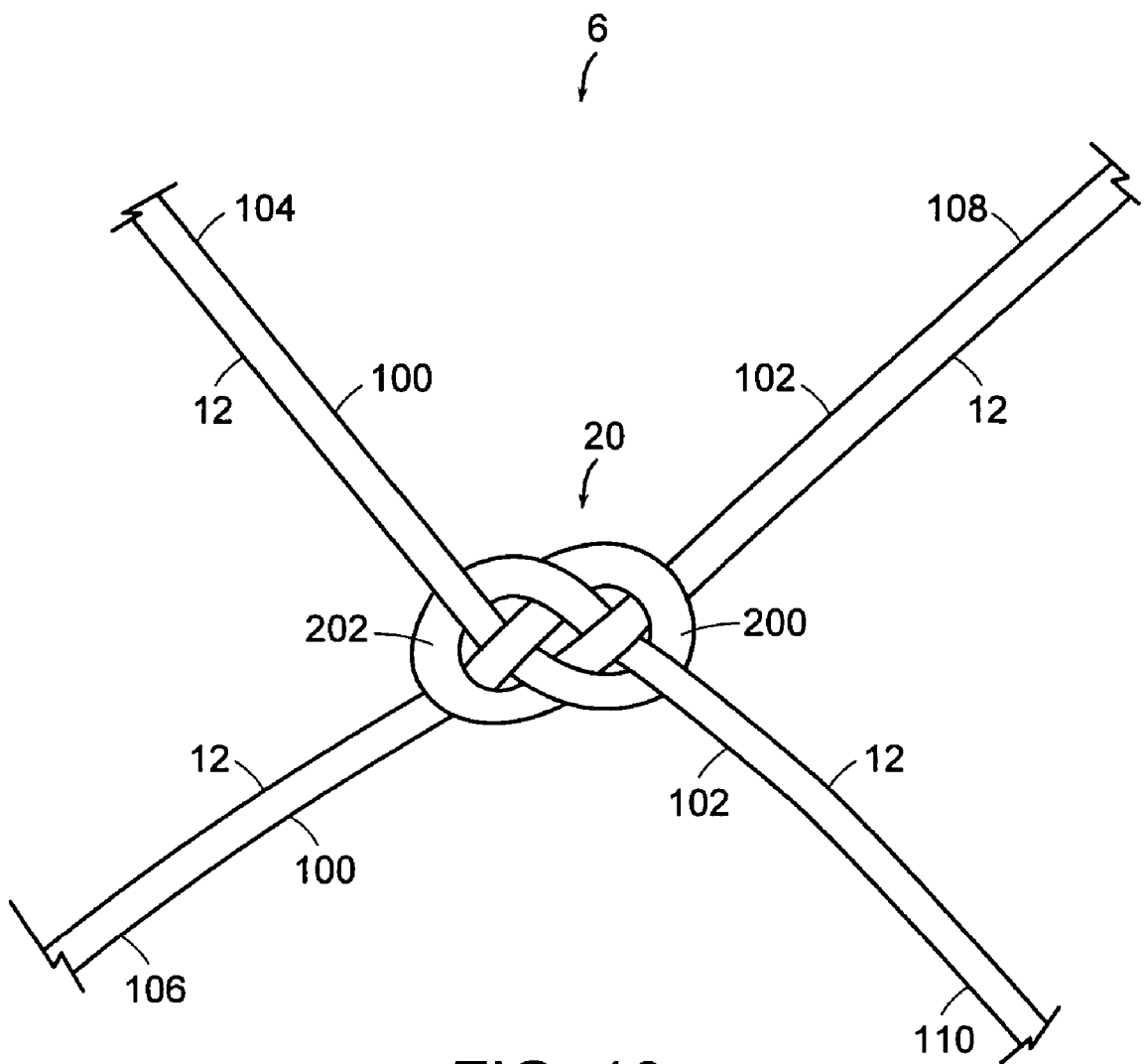
FIG. 10 depicts an end-view of a carrick bend knot at the distal end of a medical retrieval assembly according to an illustrative embodiment of the invention.
Figure 11A:
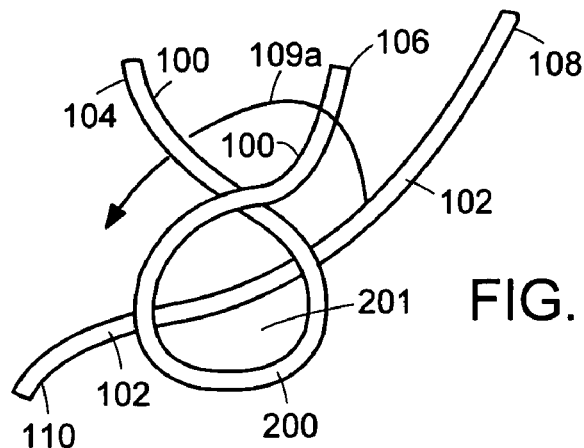
FIGS. 11A-11C depict the steps in making the carrick bend knot illustrated in FIG. 10 according to an illustrative embodiment of the invention.
Figure 11B:
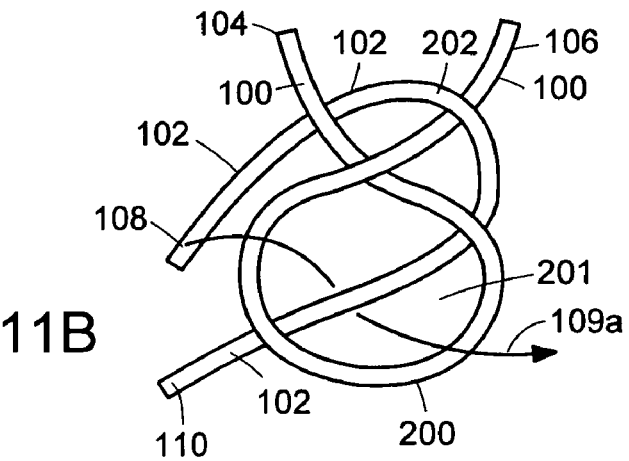
Figure 11C:
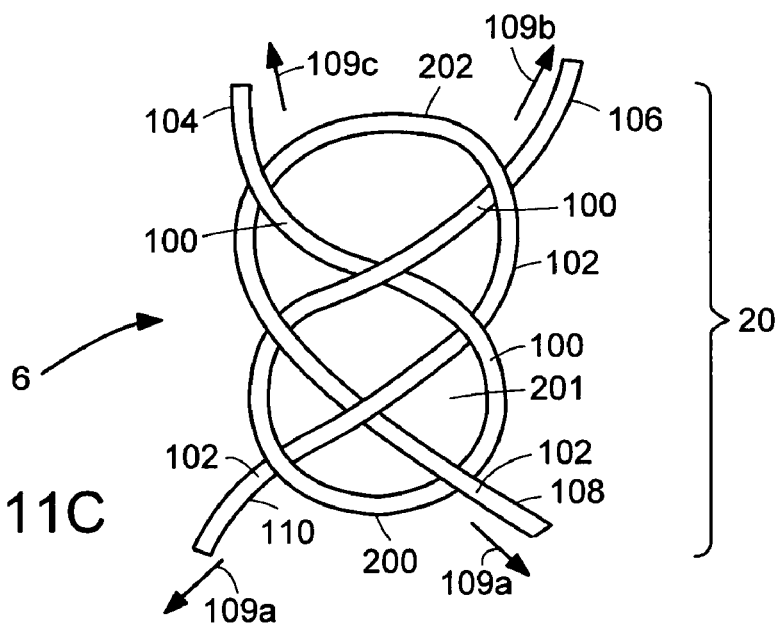

FIG. 10 depicts an end-view of a carrick bend knot at the distal end of a medical retrieval assembly according to an illustrative embodiment of the invention. In the illustrative embodiment, the ends 104, 106, 108 and 110 of the filaments 100, 102 are arranged in a symmetric, radial pattern. Alternatively, the filaments 100, 102 are arranged in an asymmetric pattern, or in some other symmetric pattern (not shown). FIGS. 11A-11C illustrate an exemplary series of steps or stages of the method used to form the carrick bend knot 20 at the distal tip 6 of the retrieval assembly 2.

FIGS. 11A-11C depict the steps in making the carrick bend knot illustrated in FIG. 10 according to an illustrative embodiment of the invention. As shown in the illustrative embodiment in FIG. 11A, the first filament 100 is bent in the first step of the method such that the second end 106 of the first filament 100 crosses the first end 104 of the first filament 100 to form a first loop 200 defining a lumen 201. Next, the first loop 200 is placed on top of the second filament 102. The second filament 102 is then bent in the direction indicated by the arrow 109a such that the first end 108 of the second filament 102 crosses the second end 106 of the first filament 100 and is placed under the first end 104 of the first filament 100 to form a second loop 202. In the illustrative embodiment depicted in FIG. 11B, the first end 108 of the second filament 102 is passed over the first filament 100, through the lumen 201 of the first loop 200, under the second filament 102, and then back through the lumen 201 of the first loop 200 as indicated by arrow 109a to exit the lumen 201 and form the carrick bend knot 20 of the distal tip 6 of the retrieval assembly 2, as depicted in FIG. 11C. Pulling the ends 104 and 106 of the first filament 100 and the ends 108 and 110 of the second filament 102 in the directions indicated by the arrows 109a, 109b, 109c, and 109d positions the first loop 200 substantially adjacent to the second loop 202 and secures the first filament 100 to the second filament 102. In a particular embodiment of the retrieval assembly, an end of filaments 100 and 102 extending from the knot 20 at the distal tip 6 can form at least a portion of a basket leg 12 as shown in FIG. 5.

Figure 12:
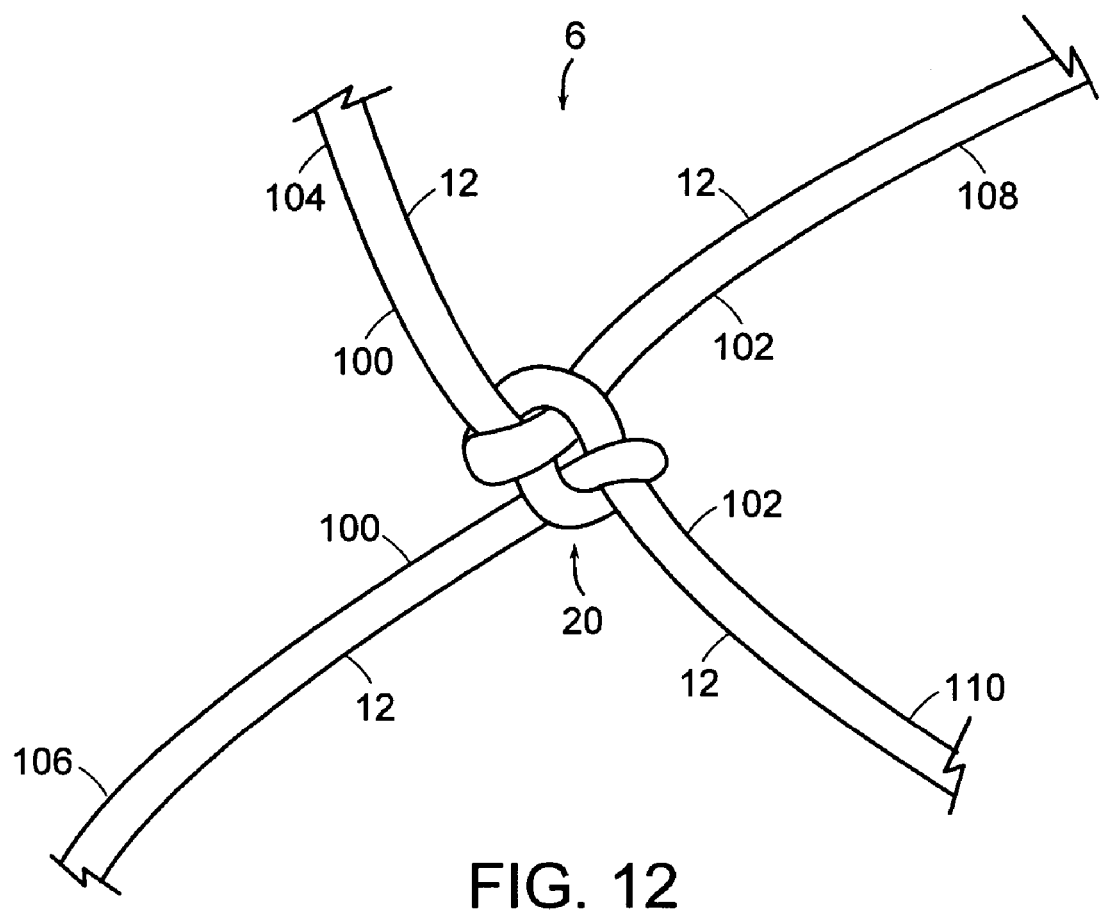
FIG. 12 depicts an end-view of another embodiment of a carrick bend knot according to an illustrative embodiment of the invention.

FIG. 12 depicts a carrick bend knot 20 at the distal end 6 of the retrieval assembly 2 according to an illustrative embodiment of the invention. A flat radial configuration carrick bend knot 20 can be made when the carrick bend knot 20 is tightened by pulling each of the first end 104 of the first filament 100 and the first end 108 of the second filament 102, and pulling the second end 106 of the first filament 100 and the second end 110 of the second filament 102 until adjacent legs 12 exit the carrick bend knot 20 in substantially perpendicular paths.

Figure 13:
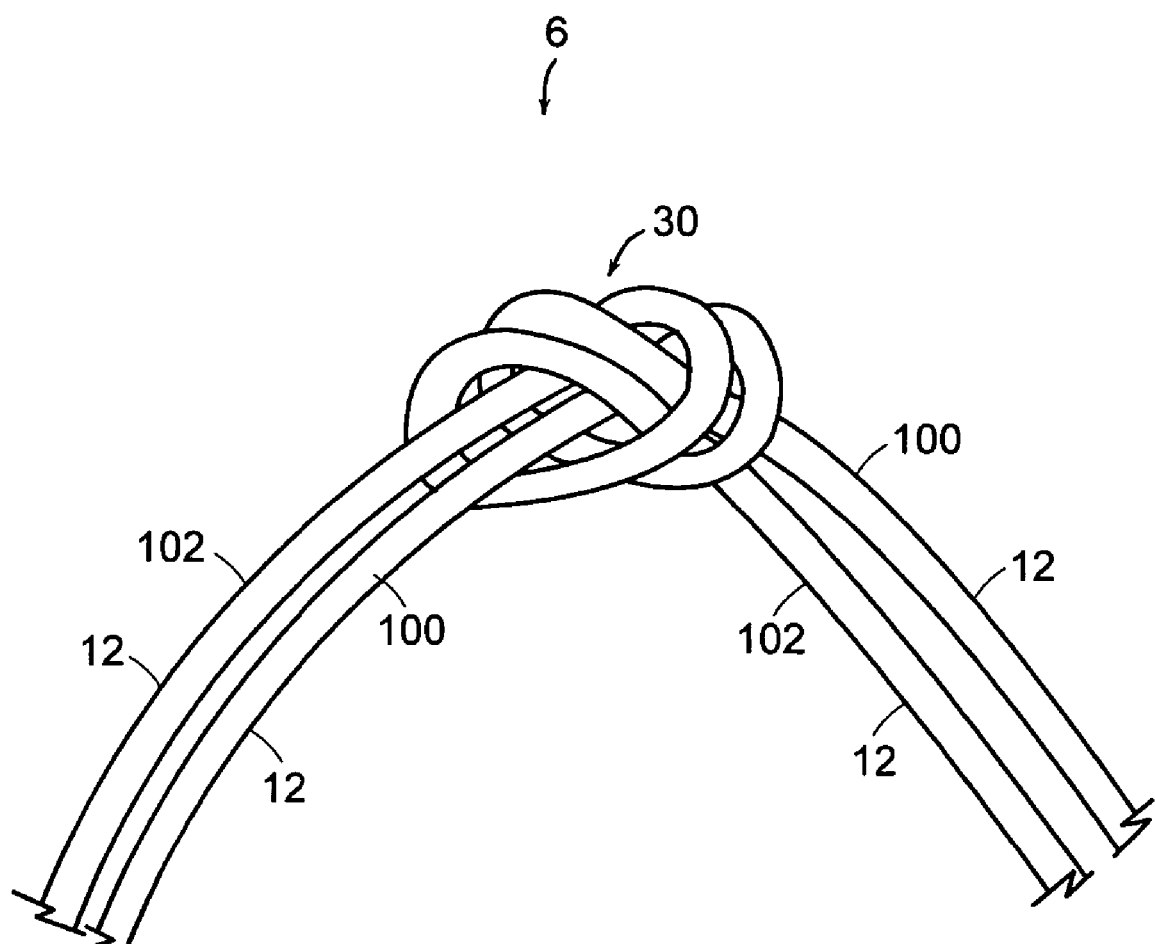
FIG. 13 depicts a side-view of a water/webbing knot at the distal end of a medical retrieval assembly according to an illustrative embodiment of the invention.
Figure 14A:
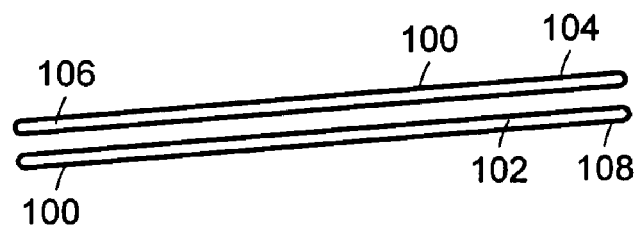
FIGS. 14A-14C depict the steps in making the water/webbing knot illustrated in FIG. 13 according to an illustrative embodiment of the invention.
Figure 14B:
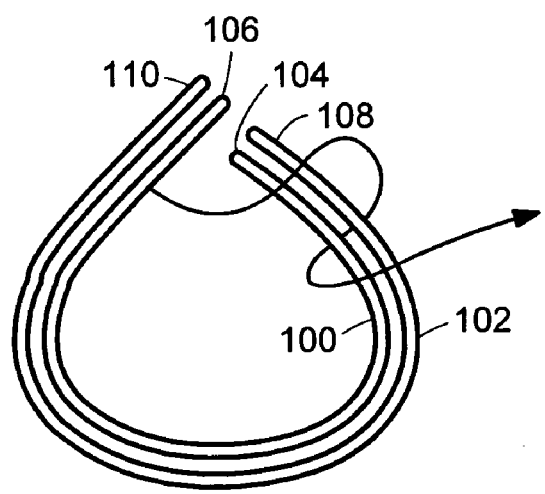
Figure 14C:
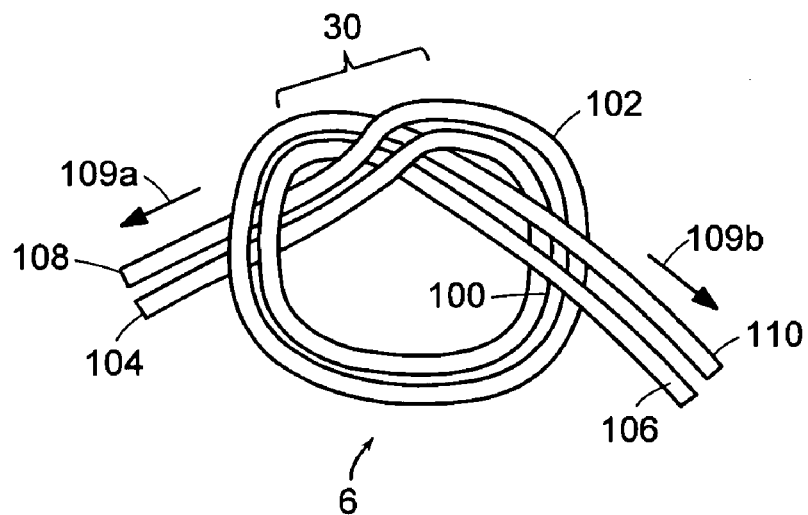

FIG. 13 depicts a knot known as a water or webbing knot 30, herein referred to as the "water/webbing" knot 30, at the distal end 6 of the retrieval assembly 2 according to an illustrative embodiment of the invention. FIGS. 14A-14C depict an exemplary series of steps of a method of making a water/webbing knot 30 to form the distal tip 6 of the medical retrieval assembly 2. Referring to FIG. 14A, the first step in forming the water/webbing knot 30 at the distal end 6 of the retrieval assembly 2 includes grouping in parallel at least a first filament 100 and a second filament 102. As shown in FIG. 14B, a single overhand knot 8 is tied in the filaments 100 and 102 to form the distal tip 6 of the retrieval assembly 2. The knot 30, depicted in FIG. 14C, can be tightened by pulling the first end 104 of the first filament 100 and the first end 108 of the second filament 102 in the direction indicated by arrow 109a, and the second end 106 of the first filament 100 and the second end 110 of the second filament 102 in the direction indicated by arrow 109b. In a particular embodiment of the retrieval assembly 2, an end of the filaments 100 and 102 extending from the knot 30 of distal tip 6 can form at least a portion of a basket leg 12 as shown in FIG. 5.

Figure 15A:
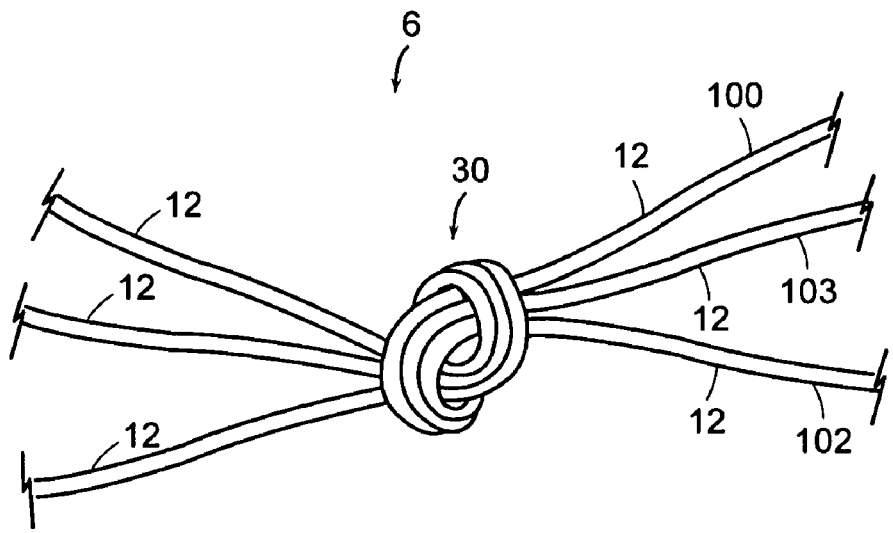
FIGS. 15A-15B depict an end-view of the water/webbing knots in which three filaments are joined together at the distal end of a medical retrieval assembly according to an illustrative embodiment of the invention.
Figure 15B:
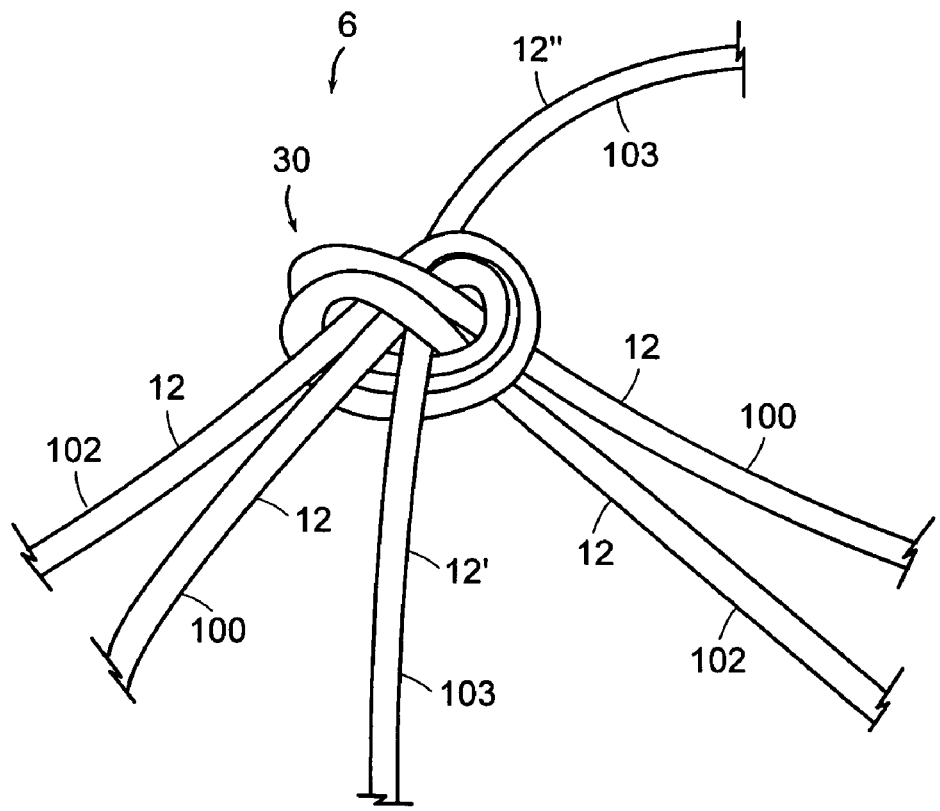

In other embodiments of the distal tip 6 of the retrieval assembly 2, more than two filaments are used to construct the atraumatic distal tip 6 including the water/webbing knot 30. In the illustrative embodiment of FIG. 15A, the water/webbing knot 30 is tied with three filaments 100, 102 and 103. The ends of the three filaments 100, 102 and 103 that extend from the water/webbing knot 30 at the distal tip 6 can be used to form all or a portion of the legs 12 of a retrieval assembly 2, including six legs 12 in a manner similar to the legs 12 of the retrieval assembly 2 including four legs 12, illustrated in FIG. 5. Alternatively, as depicted in the illustrative embodiment in FIG. 15B, additional filaments 103 can be inserted through the water/webbing knot 30 to form one or more additional legs 12', 12" of the medical retrieval assembly 2.

Figure 16:
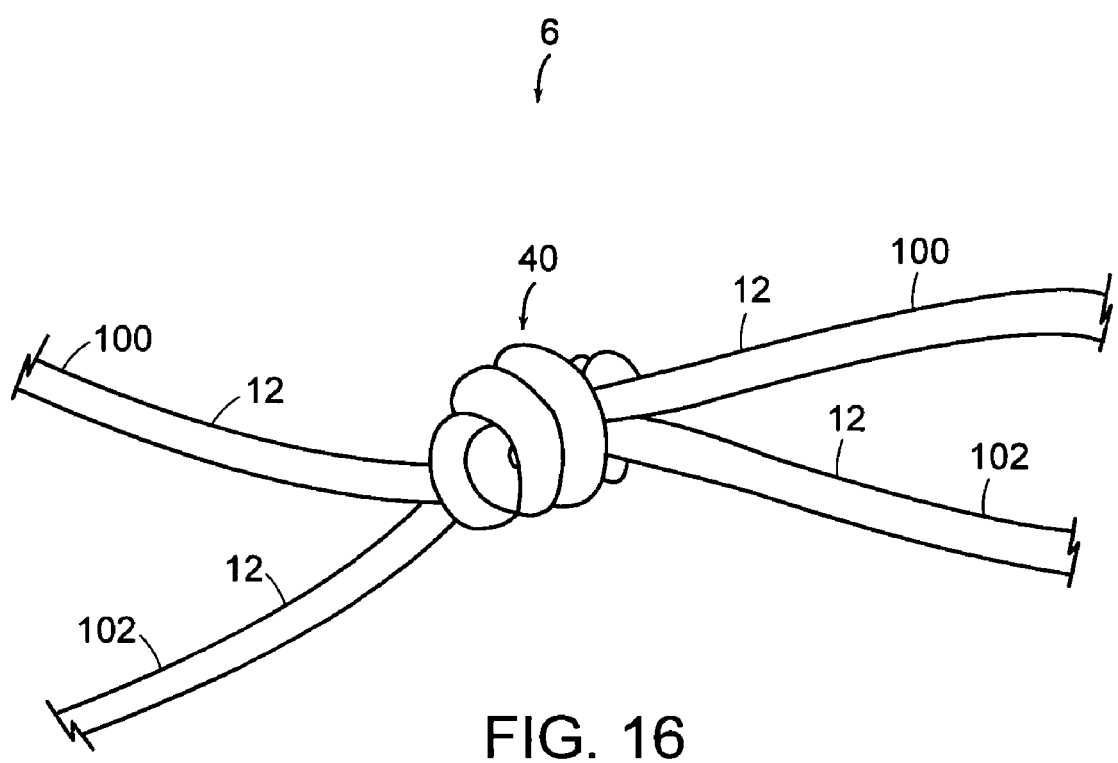
FIG. 16 depicts a barrel knot at the distal end of a medical retrieval assembly according to an illustrative embodiment of the invention.
Figure 17A:
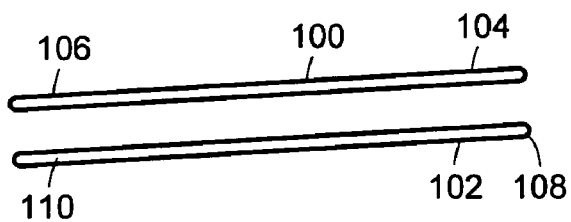
FIGS. 17A-17C depict one series of steps in making the barrel knot illustrated in FIG. 16 according to an illustrative embodiment of the invention.
Figure 17B:
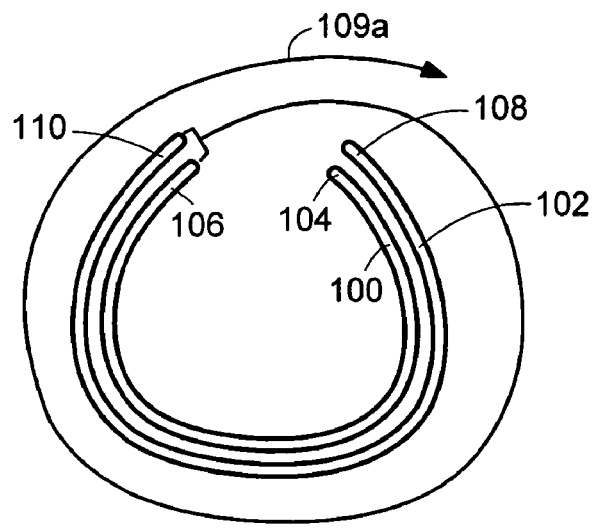
Figure 17C:
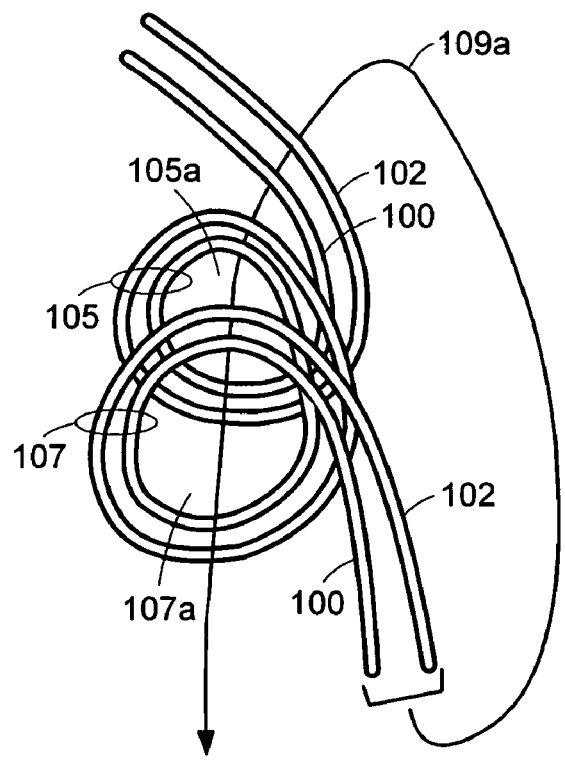

FIG. 16 depicts a barrel knot 40 at the distal tip 6 of a medical retrieval assembly 2 according to an illustrative embodiment of the invention. FIGS. 17A-17C illustrate one exemplary series of steps or stages of the method for forming the barrel knot 40 of the distal tip 6 of the retrieval assembly 2. As shown in FIG. 17A, a first filament 100 is laid parallel to and grouped with a second filament 102. As depicted in FIG. 17B, the filaments 100 and 102 are coiled together as indicated by the arrow 109a. The coiled filaments 100, 102 form two concentric loops 105 and 107 depicted in FIG. 17C. Each loop 105 and 107 defines a lumen 105a, 107a, respectively. An overhand knot, illustrated in FIG. 17C, is tied through the lumens 105a, 107a of the loops 105 and 107, respectively, in the direction indicated by the arrow 109a to secure the filaments 100 and 102 in the knot 40 and form the distal tip 6 of the retrieval assembly 2. In a particular embodiment of the retrieval assembly 2, an end of the filaments 100 and 102 extending from the barrel knot 40 at the distal tip 6 can form at least a portion of a leg 12 as shown in FIG. 5.

Figure 18A:
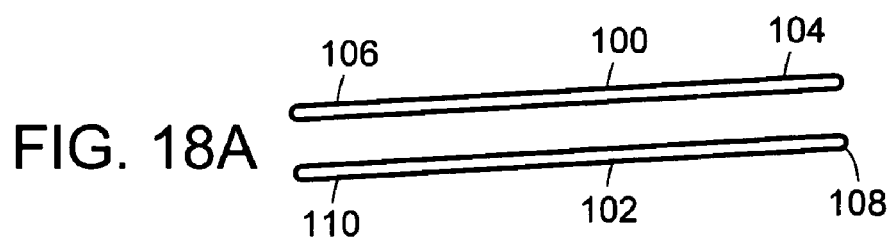
FIGS. 18A-18C depict another series of steps in making the barrel knot illustrated in FIG. 16 according to an illustrative embodiment of the invention.
Figure 18B:
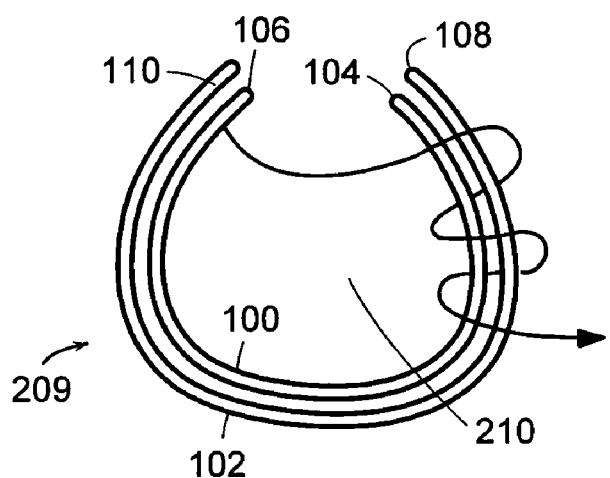
Figure 18C:
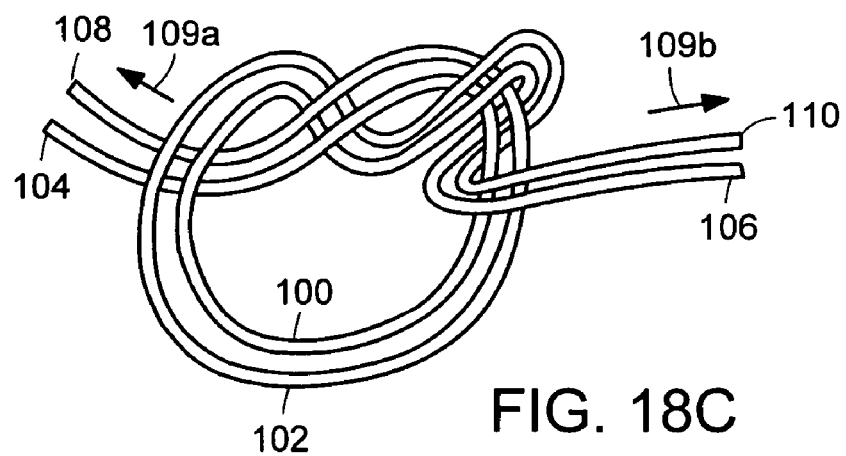

FIGS. 18A-18C illustrate an alternate exemplary series of steps or stages of the method for forming the barrel knot 40 of the distal tip 6 of the retrieval assembly 2. Referring to FIG. 18A, the first step in forming the barrel knot 40 at the distal end 6 of the retrieval assembly 2 includes grouping in parallel at least a first filament 100 and a second filament 102. As shown in FIG. 18B, the filaments 100 and 102 are bent to form a loop 209 defining a lumen 210 and the ends of the filaments 106 and 110 cross over and are wound around a portion of the grouped filaments 100 and 102 and through the lumen 210 of the loop 209 two or more times. As shown in FIG. 18C, the barrel knot 40 formed by this method can be tightened by pulling the ends of the filaments 108 and 104 in the direction indicated by arrow 109a and/or by pulling the ends of the filaments 106 and 110 in the direction indicated by arrow 109b.

Figure 19:
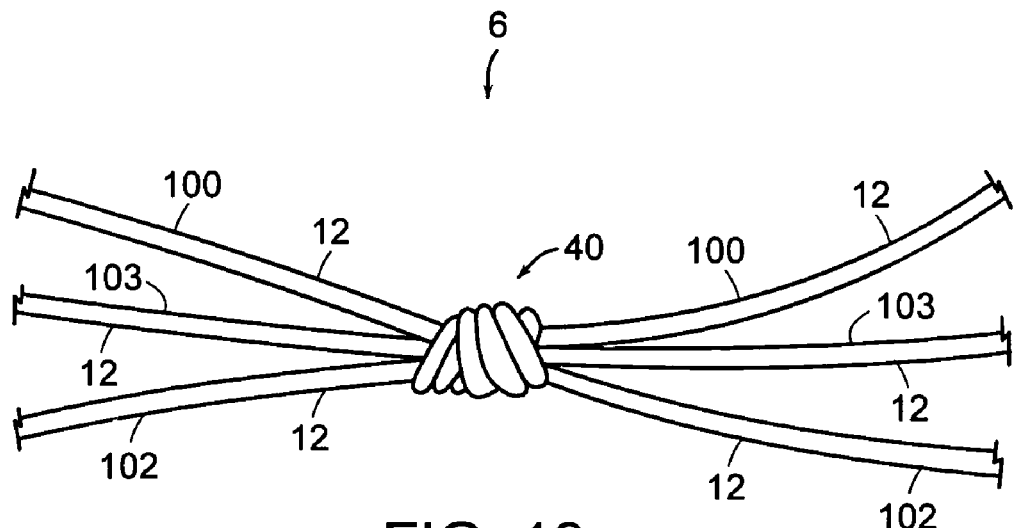
FIG. 19 depicts another barrel knot at the distal end of a medical retrieval assembly according to an illustrative embodiment of the invention.
Figure 20:
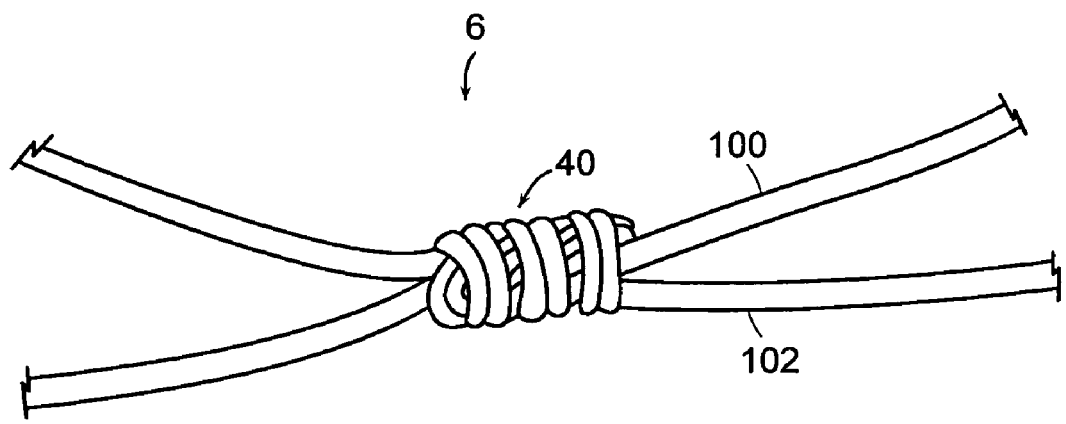
FIG. 20 depicts another barrel knot at the distal end of a medical retrieval assembly according to an illustrative embodiment of the invention.

In an alternative embodiment of the distal tip 6 of the retrieval assembly 2, more than two filaments are used to form the barrel knot 40. For example, FIG. 19 illustrates three filaments knotted in a barrel knot 40 to form the distal tip 6 of the medical retrieval assembly 2. According to the illustrative embodiment, three filaments 100, 102 and 103 are grouped together. The barrel knot 40 is tied with the three filaments 100, 102 and 103 at the distal tip 6 of the retrieval assembly 2. This embodiment of the barrel knot 40 features six legs 12 extending from the distal tip 6. In yet other embodiments, such as that illustrated in FIG. 20, the distal tip 6 of the medical retrieval assembly 2 is constructed by coiling the filaments 100 and 102 to form more than two loops, for example three loops, each loop defining a lumen. An overhand knot is tied with the filaments 100 and 102 through the lumens of the three loops to form the three-loop barrel knot 40 illustrated in FIG. 20.

Figure 21:
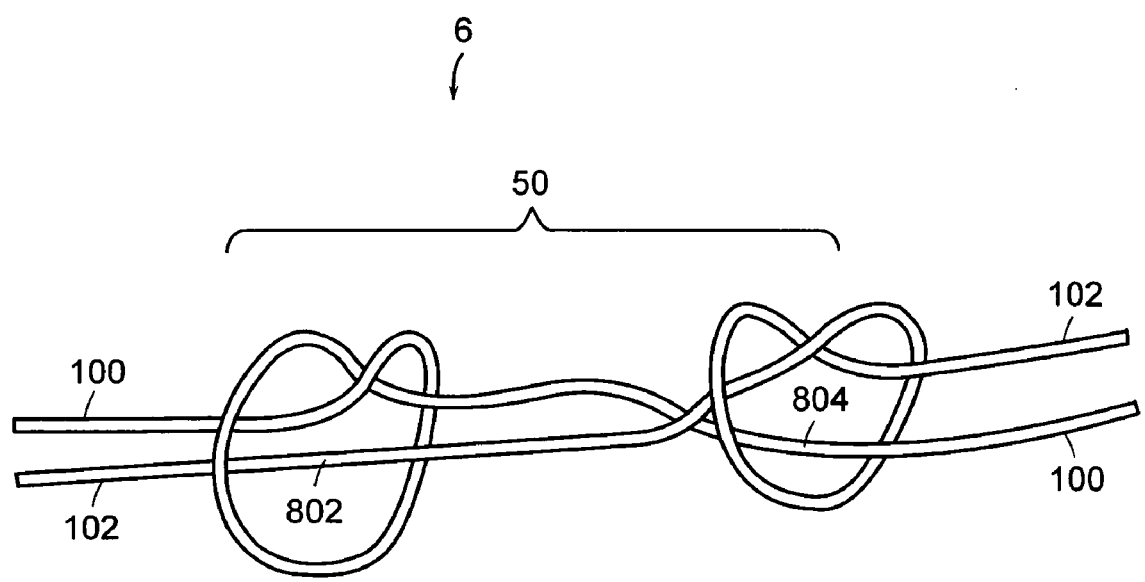
FIG. 21 depicts a fisherman's knot at the distal end of a medical retrieval assembly according to an illustrative embodiment of the invention.
Figure 22A:
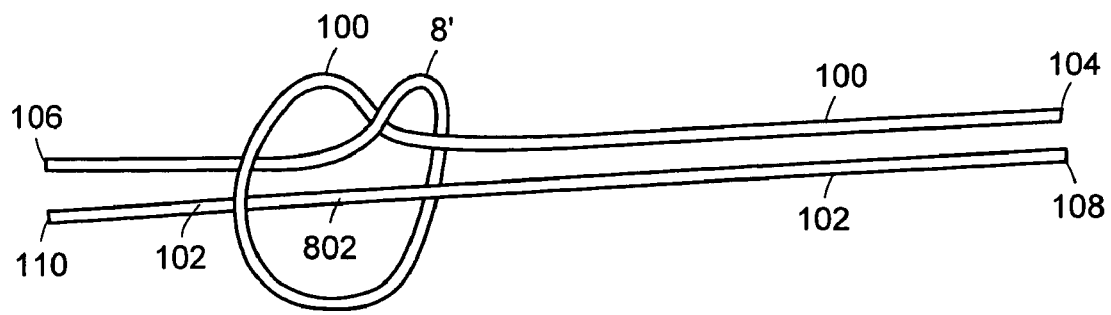
FIGS. 22A-22B depict one series of steps in making the fisherman's knot in FIG. 20 according to an illustrative embodiment of the invention.
Figure 22B:
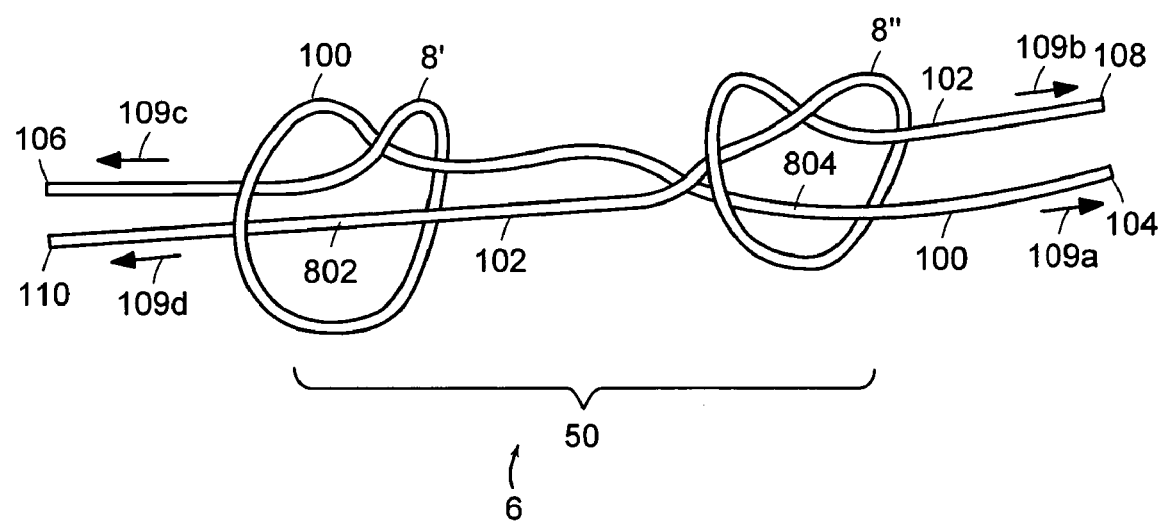

FIG. 21 depicts a fisherman's knot 50 at the distal end 6 of a retrieval assembly 2 according to an illustrative embodiment of the invention. FIGS. 22A and 22B illustrate an exemplary series of steps or stages of the method to form the fisherman's knot 50 at the distal tip of the retrieval assembly 2. As shown in the illustrative embodiment of FIG. 22A, a first overhand knot 8' is tied in the first filament 100 onto a first position 802 of the second filament 102. The first position 802 is located anywhere along the length of the second filament 102. As shown in the illustrative embodiment of FIG. 22B, a second overhand knot 8" is tied in the second filament 102 onto a second position 804 of the first filament 100 to form the distal tip 6 of the retrieval assembly 2. The second position 804 is located at a position on the first filament 100 that is not knotted. The fisherman's knot 50 can be tightened by pulling the first end 104 of the first filament 100, the first end 108 of the second filament 102, the second end 106 of the first filament 100, and the second end 110 of the second filament 102, in the directions indicated by the arrows 109a, 109b, 109c, 109d, respectively. In a particular embodiment of the retrieval assembly 2, an end of the filaments 100 and 102 extending from the fisherman's knot 50 at the distal tip 6 can form at least a portion of a leg 12 as shown in FIG. 5.

Figure 23:
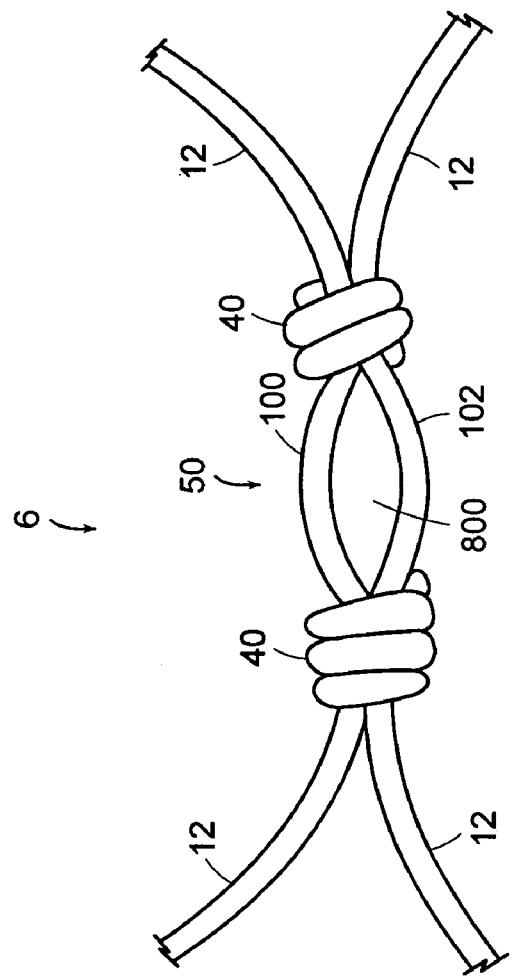
FIG. 23 depicts a fisherman's knot at the distal end of a medical retrieval assembly according to another illustrative embodiment of the invention.

FIG. 23 depicts a modified fisherman's knot 50 at the distal tip 6 of a retrieval assembly 2 according to an illustrative embodiment of the invention. According to an exemplary embodiment of the invention, the modified fisherman's knot 50 at the distal tip 6 of the medical retrieval assembly 2 is constructed by the barrel knot method, described above and shown in FIGS. 18A-18C. For example, to make the modified fisherman's knot 50 depicted in FIG. 23, the barrel knot method is repeated at least twice with the filaments 100, 102 to create at least two independent barrel knots 40 along the filaments 100 and 102.

In the illustrative embodiment shown in FIG. 23, the individual barrel knots 40 are spaced apart, for example, by a center portion 800 of the fisherman's knot 50.

Figure 25:
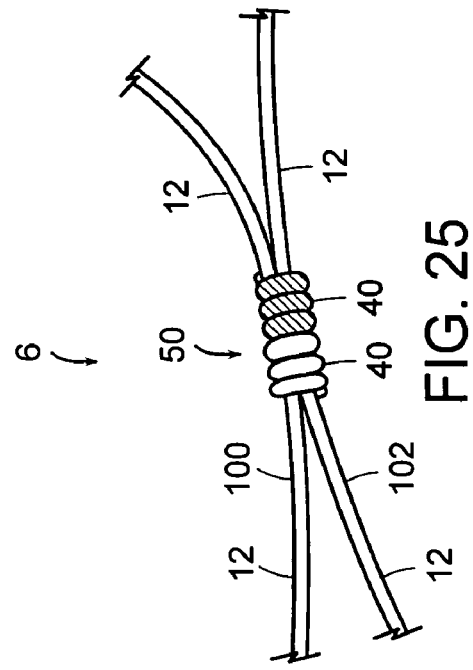
FIG. 25 depicts a fisherman's knot at the distal end of a medical retrieval assembly according to yet another illustrative embodiment of the invention.
Figure 24:
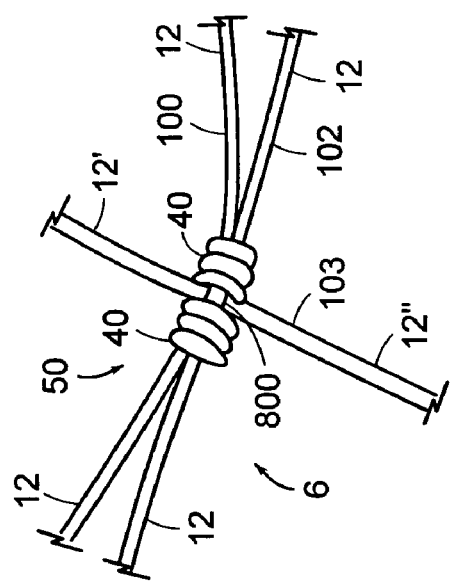
FIG. 24 depicts a fisherman's knot at the distal end of a medical retrieval assembly according to still another illustrative embodiment of the invention.

FIG. 24 depicts a fisherman's knot 50 according to another illustrative embodiment of the invention. In the illustrative embodiment, the fisherman's knot 50 includes additional legs 12', 12", which are constructed by inserting one or more filaments 103 through the center portion 800. Alternatively, in the illustrative embodiment shown in FIG. 25, the distal tip 6 features a fisherman's knot 50 in which the independent barrel knots 40 are placed adjacent to each other.

In further embodiments, the distal tip 6 includes a fisherman's knot 50 formed from more than two filaments. For example, three filaments may be used to form the fisherman's knot 50 by adding a third overhand knot in the third filament in a manner similar to the first and second overhand knots 8', 8" described above with respect to the fisherman's knot 50. In this embodiment, the two ends of each of the three filaments may form six retrieval assembly legs (not shown).

Figure 26:
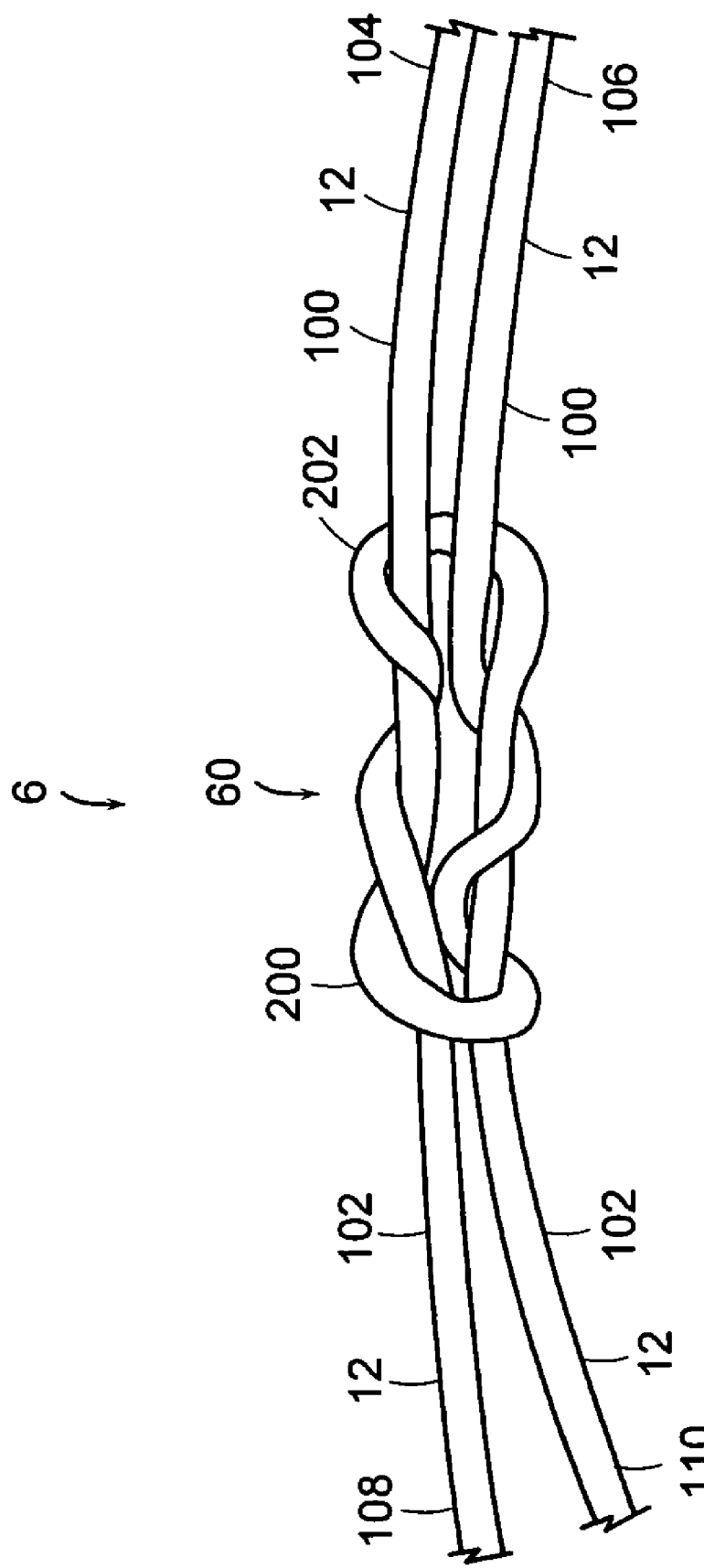
FIG. 26 depicts a surgeon's knot at the distal end of a medical retrieval assembly according to an illustrative embodiment of the invention.
Figure 27A:
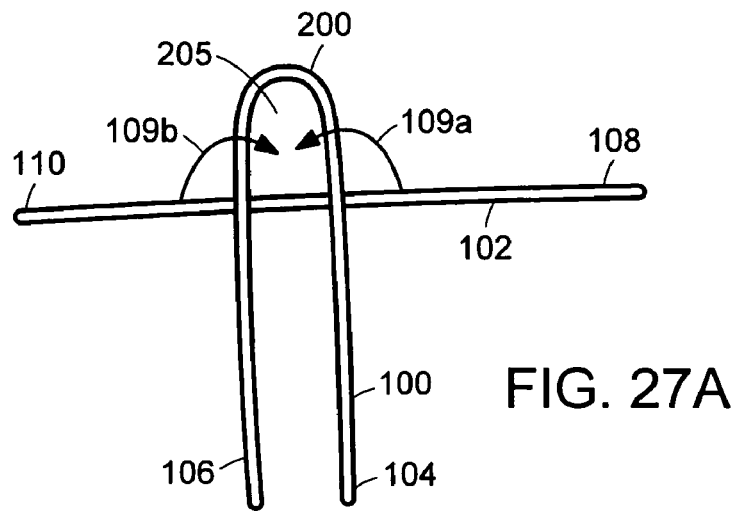
FIGS. 27A-27C depict one series of steps in making the surgeon's knot in FIG. 25 according to an illustrative embodiment of the invention.
Figure 27B:
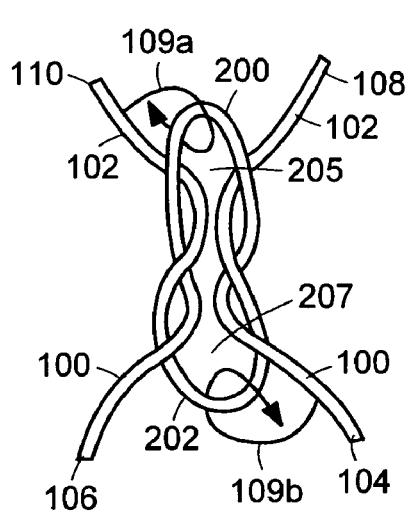
Figure 27C:
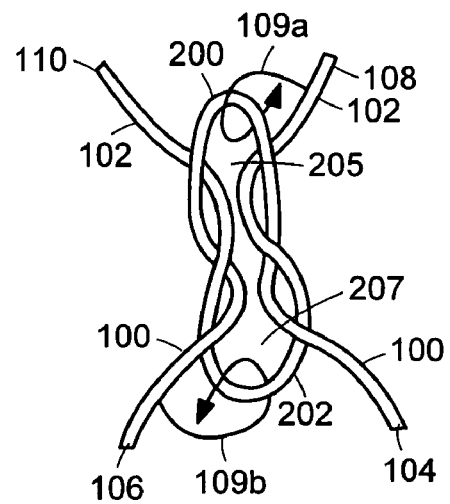

FIG. 26 depicts a surgeon's knot 60 at the distal tip 6 of the retrieval assembly 2 according to an illustrative embodiment of the invention. FIGS. 27A-27C illustrate an exemplary series of stages or steps of the first method of forming the surgeon's knot 60 at the distal tip 6 of the retrieval assembly 2. As shown in the illustrative embodiment of FIG. 27A, the first filament 100 is bent to form a first loop 200 defining a lumen 205. The first loop 200 is laid on top of and substantially perpendicular to the second filament 102. The first end 108 and the second end 110 of the second filament 102 are placed through the lumen 205 of the first loop 200 in the direction indicated by the arrows 109a, 109b in FIG. 27A to form a second loop 202 defining a lumen 207, depicted in FIG. 27B. The first end 106 of the second filament 102 is wound through the lumen 205 of the first loop 200 and around the first filament 102 in the direction as indicated by arrow 109a. The second end 106 of the first filament 100 is wound through the lumen 207 of the second loop 202 and around the second filament 102 in the direction indicated by arrow 109b.

FIG. 27C depicts a surgeon's knot 60 at the distal tip 6 of a retrieval assembly 2 according to another illustrative embodiment of the invention. In the illustrative embodiment, the first surgeon's knot method includes winding the first end 108 of the second filament 102 through the lumen 205 of the first loop 200 and around the first filament 100, and winding the second end 106 of the first filament 100 through the lumen 207 of the second loop 202 and around the second filament 102, in the directions indicated by the arrows 109a, 109b in FIG. 27C. In a particular embodiment according to the invention, an end of the filaments 100 and 102 extending from the surgeon's knot 60 at the distal tip 6 can form at least a portion of a leg 12 as shown in FIG. 5.

Figure 28:
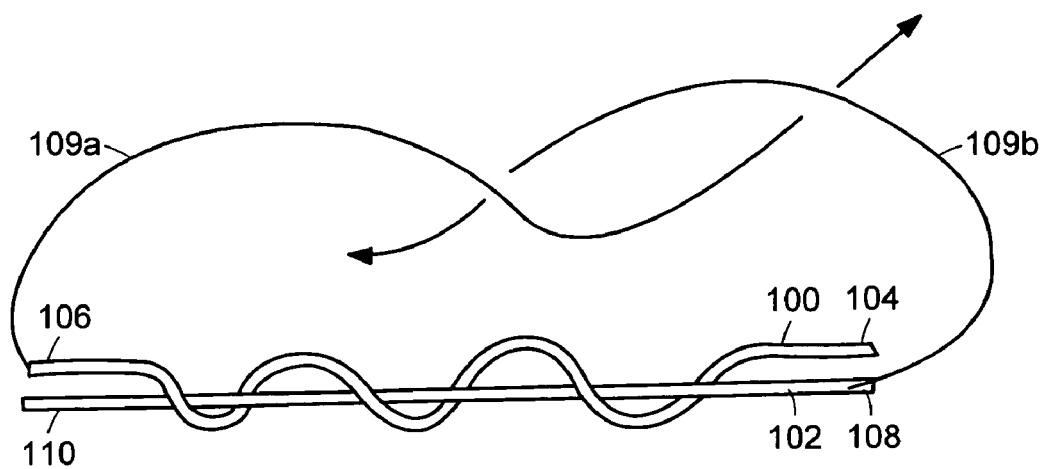
FIG. 28 depicts another series of steps in making the surgeon's knot illustrated in FIG. 25 according to another illustrative embodiment of the invention.

FIG. 28 depicts a surgeon's knot 60 at the distal tip 6 of a medical retrieval assembly 2 according to an illustrative embodiment of the invention. The surgeon's knot 60 is constructed by the steps set forth in FIG. 28, herein referred to as the second surgeon's knot method. The second surgeon's knot method includes winding a first filament 100 around a second filament 102 at least three times and tying an overhand knot using the first end 108 of the second filament 102 and the second end 106 of the first filament 100, in the direction indicated by the arrows 109a, 109b in FIG. 28.

Regardless of whether the first surgeon's knot method or the second surgeon's knot method is used to construct the distal tip 6 of the medical retrieval assembly 2, the first filament 100 and the second filament 102 can be wound around each other more than three times, for example, four times as illustrated in FIG. 29A, and six times as illustrated in FIG. 29B.

In other embodiments, a medical retrieval device 7 can have a retrieval assembly 2 constructed from the same or a combination of knots according to the invention. Alternatively, the knots and methods of the invention can be utilized for any device which requires the joining of filaments.

In another aspect, the invention relates to a method for retrieving material from a body, such as a body tract or body canal. Material (e.g., biological or foreign) can be retrieved from a body by using a retrieval assembly 2 according to the invention with an atraumatic tip that is formed by knotting together filaments 100, 102 at the distal end 6 of the retrieval assembly 2. The retrieval assembly 2 has a distal tip 6 that is atraumatic, thus allowing the capture of material that is located in pockets such as the renal calyx or other difficult-to-access areas within the body. Because the distal tip 6 is atraumatic, the retrieval assembly 2 can make intimate contact with the surface of tissue, even the walls or lining of a pocket-type area, and allow the retrieval of stones or other materials that are unrecoverable with conventional tipped retrieval assemblies that can cause tissue trauma and are limited in how close the retrieval assembly can get to the tissue because of the existence of the protruding tip.

A method for retrieving material from a body includes inserting a retrieval device 7 according to the invention into the body, moving the retrieval assembly 2 into the unrestrained position by withdrawing the sheath 14 from the retrieval assembly 2 with the retrieval assembly 2 in a stationary position, or by extending the retrieval assembly 2 outside the sheath 14 with the sheath 14 in a stationary position. The retrieval assembly 2 is maneuvered via the actuator 4 on the handle 16 (which is located outside of the body) of the retrieval device 7 until the material (e.g., stone) is entrapped within the three-dimensional retrieval assembly 2, and the material is captured within the retrieval assembly 2 by moving the retrieval assembly 2 relative to the sheath 14 by any of the above disclosed mechanisms to close the legs 12 of the retrieval assembly 2 around the material. With the material held by the retrieval assembly 2, the medical retrieval device 7, including the retrieval assembly 2, can be withdrawn from the body to remove the material from the body. In one embodiment of the method, before the retrieval assembly 2 is withdrawn from the body with the captured material, the material can be broken apart by, for example, laser energy or mechanical lithotripsy. Mechanisms for breaking up the material before its removal from the body can be part of the retrieval device 7 or can be separate tools/devices that are also inserted into the body and utilized at the appropriate time to break apart the material. The materials that can be captured with retrieval assemblies 2 according to the invention include tumors, for example, a polyp, or a stone, such as a kidney stone, a ureteral stone, a urinary bladder stone, a gall bladder stone, or a stone within the biliary tree.

Variations, modifications, and other implementations of what is described herein will occur to those of ordinary skill without departing from the spirit and the scope of the invention. Accordingly, the invention is not to be limited only to the preceding illustrative description.

What is claimed is:

1. A medical retrieval device, comprising:
   a sheath; and
   a retrieval assembly comprising a plurality of filaments knotted together in a flipped double overhand knot to form a knotted distal end of the retrieval assembly, the plurality of filaments arranged in a symmetric, radial pattern, the retrieval assembly being collapsed when restrained by the sheath and expanded when unrestrained by the sheath.

2. The medical retrieval device of claim 1, wherein the flipped double overhand knot comprises:
   (a) a first filament comprising a first end and a second end;
   (b) a second filament comprising a first end and a second end;
   (c) the second filament placed across and substantially perpendicular to the first filament;
   (d) the second end of the first filament placed across the first end of the first filament and a first overhand knot tied with the first filament around the second filament; and
   (e) the second end of the second filament placed across the first end of the second filament and a second overhand knot tied with the second filament around the first filament to form the flipped double overhand knot at the knotted distal end of the retrieval assembly.

3. The medical retrieval device of claim 2, wherein, at a distal end view of the retrieval assembly, the first end of the first filament exits the first overhand knot under the first filament, and at the distal end view of the retrieval assembly, the first end of the second filament exits the second overhand knot under the second filament and adjacent to the first end of the first filament.

4. The medical retrieval device of claim 1, wherein the knotted distal end does not include an adhesive.

5. The medical retrieval device of claim 1, wherein the knotted distal end includes an adhesive.

6. The medical retrieval device of claim 1, wherein at least one filament forms two legs of the retrieval assembly.

7. A medical retrieval device, comprising:
   a sheath; and
   a retrieval assembly comprising a plurality of filaments knotted together in a carrick bend knot to form a knotted distal end of the retrieval assembly, the retrieval assembly being collapsed when restrained by the sheath and expanded when unrestrained by the sheath.

8. The medical retrieval device of claim 7, wherein the carrick bend knot comprises:
   (a) a first filament comprising a first end and a second end;
   (b) a second filament comprising a first end and a second end;
   (c) the first filament bent wherein the second end of the first filament crosses the first end of the first filament to form a first loop defining a lumen;
   (d) the first loop placed on top of the second filament;
   (e) the second filament bent wherein the first end of the second filament crosses the second end of the first filament and is placed under the first end of the first filament to form a second loop;
   (f) the first end of the second filament placed through the lumen of the first loop and under the second filament; and
   (g) the first end of the second filament pulled through the lumen of the first loop to form the carrick bend knot at the knotted distal end of the retrieval assembly.

9. The medical retrieval device of claim 7, wherein the knotted distal end does not include an adhesive.

10. The medical retrieval device of claim 7, wherein the knotted distal end includes an adhesive.

11. The medical retrieval device of claim 7, wherein the ends of the plurality of filaments are arranged in an asymmetric, radial pattern.

12. The medical retrieval device of claim 7, wherein the ends of the plurality of filaments are arranged in a symmetric, radial pattern.

13. The medical retrieval device of claim 7, wherein at least one filament forms two legs of the retrieval assembly.

14. A retrieval assembly, comprising: a flipped double overhand knot, comprising
   (a) a first filament comprising a first end and a second end;
   (b) a second filament comprising a first end and a second end;
   (c) the second filament placed across and substantially perpendicular to the first filament;
   (d) the second end of the first filament placed across the first end of the first filament and a first overhand knot tied with the first filament around the second filament;
   (e) the second end of the second filament placed across the first end of the second filament and a second overhand knot tied with the second filament around the first filament to form the flipped double overhand knot at the knotted distal end of the retrieval assembly, wherein the ends of the first and second filaments are arranged in a symmetric, radial pattern.

15. The retrieval assembly of claim 14, wherein the flipped double overhand knot does not include an adhesive.

16. The retrieval assembly of claim 14, wherein the flipped double overhand knot includes an adhesive.

17. The retrieval assembly of claim 14, wherein at least one filament forms two legs of the retrieval assembly.

18. The retrieval assembly of claim 14, wherein, at a distal end view of the retrieval assembly, the first end of the first filament exits the first overhand knot under the first filament, and at the distal end view of the retrieval assembly, the first end of the second filament exits the second overhand knot under the second filament and adjacent to the first end of the first filament.

19. A retrieval assembly, comprising:
a carrick bend knot, comprising
(a) a first filament comprising a first end and a second end;
(b) a second filament comprising a first end and a second end;
(c) the first filament bent wherein the second end of the first filament crosses the first end of the first filament to form a first loop defining a lumen;
(d) the first loop placed on top of the second filament;
(e) the second filament bent wherein the first end of the second filament crosses the second end of the first filament and is placed under the first end of the first filament to form a second loop;
(f) the first end of the second filament placed through the lumen of the first loop and under the second filament; and
(g) the first end of the second filament pulled through the lumen of the first loop to form the carrick bend knot at the knotted distal end of the retrieval assembly.

20. The retrieval assembly of claim 19, wherein the carrick bend knot does not include an adhesive.

21. The retrieval assembly of claim 19, wherein the carrick bend knot includes an adhesive.

22. The retrieval assembly of claim 19, wherein at least one filament forms two legs of the retrieval assembly.

* * * * *

UNITED STATES PATENT AND TRADEMARK OFFICE
CERTIFICATE OF CORRECTION

| | | |
|---|---|---|
| PATENT NO. | : 7,491,211 B2 | Page 1 of 1 |
| APPLICATION NO. | : 10/853052 | |
| DATED | : February 17, 2009 | |
| INVENTOR(S) | : Ziegler | |

It is certified that error appears in the above-identified patent and that said Letters Patent is hereby corrected as shown below:

Title page, item (*) Notice: Subject to any disclaimer, the term of this patent is extended or adjusted under 35 U.S.C. 154(b) by 780 days.

Delete the phrase "by 780 days" and insert -- by 1303 days --.

Signed and Sealed this

Twenty-fourth Day of August, 2010

David J. Kappos
*Director of the United States Patent and Trademark Office*